United States Patent
Henrique et al.

(10) Patent No.: US 9,534,019 B2
(45) Date of Patent: Jan. 3, 2017

(54) **PEPTIDES WITH ANTIMICROBIAL ACTIVITY, DRUG COMPOSITIONS FOR THE TREATMENT AND PROPHYLAXIS OF ANIMALS, COMPOSITIONS FOR THE TREATMENT AND PROPHYLAXIS OF PLANTS, USES OF SAID PEPTIDES, AND USES OF *PAENIBACILLUS ELGII OUROFINENSIS* EXTRACT**

(71) Applicants: OURO FINO PARTICIPAÇÕES E EMPREENDIMENTOS S/A, Ribeirão Preto (BR); UNIÃO BRASILIENSE DE EDUCÃçO E CULTURA—UBEC, Silvânia (BR)

(72) Inventors: Carlos Henrique Henrique, Ribeirão Preto (BR); Janaina Fernandez De Araújo, Brasília (BR); Alinne Pereira De Castro, Brasília (BR); Lucas Carvalho, Gama (BR); Octávio Luis Franco, Brasília (BR); Adriane Kurokawa Silva, Brasília (BR); Ricardo Henrique Kruger, Brasília (BR)

(73) Assignees: OURO FINO PARTICIPAÇÕES EMPREENDIMENTOS S/A (BR); UNIÃO BRASILIENSE DE EDUCÃçO E CULTURA—UBEC (BR)

( * ) Notice: Subject to any disclaimer, the term of this patent is extended or adjusted under 35 U.S.C. 154(b) by 0 days.

(21) Appl. No.: 14/686,417

(22) Filed: Apr. 14, 2015

(65) Prior Publication Data
US 2015/0218226 A1    Aug. 6, 2015

Related U.S. Application Data

(63) Continuation-in-part of application No. 14/111,707, filed as application No. PCT/BR2011/000104 on Apr. 12, 2011, now abandoned.

(51) Int. Cl.
| A01N 37/18 | (2006.01) |
| A61K 38/04 | (2006.01) |
| A61K 38/12 | (2006.01) |
| C07K 11/02 | (2006.01) |
| A01N 63/02 | (2006.01) |
| C07K 7/56 | (2006.01) |
| A61K 38/00 | (2006.01) |

(52) U.S. Cl.
CPC ............ *C07K 11/02* (2013.01); *A01N 63/02* (2013.01); *A23K 10/12* (2016.05); *A23K 20/147* (2016.05); *A23K 50/30* (2016.05); *A23K 50/75* (2016.05); *C07K 7/56* (2013.01); *A61K 38/00* (2013.01)

(58) Field of Classification Search
None
See application file for complete search history.

(56) References Cited

U.S. PATENT DOCUMENTS

| 4,294,754 A | 10/1981 | Takahara et al. |
| 7,935,335 B2 * | 5/2011 | Kochi ............... A01N 63/00 424/93.1 |

FOREIGN PATENT DOCUMENTS

| BR | PI0908664 | 2/2012 |
| JP | 56096669 A | 8/1981 |

OTHER PUBLICATIONS

Wu XC et al.: "Isolation and partial characterization of antibiotics produced by Paenibacillus elgii B69." FEMS Microbiol Lett. vol. 310, No. 1, Jun. 16, 2010, pp. 32-38.
Dal-Soo Kim et al.: "Paenibacillus elgii SD17 as a Biocontrol Agent Against Soil-borne Turf Diseases." Plant Pathol. J. vol. 21, No. 4, 2005, pp. 328-333, published 2005.
Kim DS et al.: "*Paenibacillus elgii* sp. nov., with broad antimicrobial activity." Int J Syst Evol Microbiol vol. 54, Nov. 2004, pp. 2031-2035, published in Nov. 2004.
PCT/BR2011/000104 International Search Report dated Mar. 7, 2012.
Sugawara K et al.: "BMY-28160 A New Peptide Antibiotic." J Antibiotics (Tokyo), vol. 37 No. 10, pp. 1257-1259, published in Oct. 1984.
Takahara Y et al.: Isolation of a New Peptide Antibiotic, Permetin A, from Bacillus Circulans. J Antibiotics (Tokyo), vol. 32 No. 2, pp. 115-120, published in Feb. 1979.

* cited by examiner

*Primary Examiner* — Marcela M Cordero Garcia
(74) *Attorney, Agent, or Firm* — Hahn Loeser & Parks, LLP

(57) ABSTRACT

The present invention provides methods of preparing extracts of material fermented with *Paenibacillus* sp., preferably *Paenibacillus elgii ourofinensis*. The extracts exhibit antimicrobial activity and may be used in the treatment or prophylaxis of infections in animals or plants or as a growth promoter in animals intended for slaughter for human consumption. The invention provides new peptides derived from the fractions of the fermentation of *Paenibacillus elgii ourofinensis* extract, prepared for example, by n-butanol extraction of the *Paenibacillus* fermentation broth. The extract may optionally be dried and/or mixed with other components such as appropriate nutritional components to form an animal feed, additional therapeutic adjuvants, or pharmaceutically or agriculturally acceptable carriers. The invention is also related to the isolation of this strain of *Paenibacillus*, including fermentation in a medium such as corn steep liquor and selection of catalase negative bacteria.

20 Claims, 9 Drawing Sheets

Chemical Formula: $C_{54}H_{93}N_{12}O_{12}^+$
Exact Mass: 1101.70304 a)

b)

a) b)

a)

b)

PEPTIDES WITH ANTIMICROBIAL ACTIVITY, DRUG COMPOSITIONS FOR THE TREATMENT AND PROPHYLAXIS OF ANIMALS, COMPOSITIONS FOR THE TREATMENT AND PROPHYLAXIS OF PLANTS, USES OF SAID PEPTIDES, AND USES OF *PAENIBACILLUS ELGII OUROFINENSIS* EXTRACT

CROSS REFERENCE TO RELATED APPLICATIONS

This application is a continuation-in-part application of co-pending U.S. application Ser. No. 14/111,707 filed 31 Dec. 2013, which is a U.S. National Stage application of PCT/BR2011/000104, filed 12 Apr. 2011.

INCORPORATION BY REFERENCE OF MATERIAL SUBMITTED ELECTRONICALLY

The material contained in the Sequence Listing provided herewith in ASCII compliant format in the text file entitled "210568-00005_ST25.txt" created on Mar. 11, 2015 and containing 2,659 bytes, is hereby incorporated by reference herein.

FIELD OF THE INVENTION

The present invention relates to a lipopeptide with antimicrobial activity and growth-promoting activity of organisms, especially plants and animals. The lipopeptides of the invention were identified from extracts of the culture of bacterial isolate of the genus *Paenibacillus*, more specifically the isolate of *Paenibacillus elgii*. The invention further relates to the use of the isolate *Paenibacillus* extract as a growth promoter and in the treatment and prophylaxis of organisms, such as plants and animals. The invention further relates to the use of the peptides of the invention as a growth promoter and in the treatment and prophylaxis of organisms, such as plants and animals. Additionally, the present invention relates to drug compositions for the treatment and prophylaxis of animals, said composition comprising a therapeutically or prophylactically effective amount of the peptides of the invention in association with a pharmaceutically acceptable carrier or excipient.

BACKGROUND OF THE INVENTION

Antibiotics are the most exploited microbial products in the biotechnology industry. Currently, the technology used for the treatment of veterinary infections and in the promotion of animal growth is based on conventional antibiotics. For example, it was shown that the bacteria *Bacillus subtilis, Escherichia coli* and *Salmonella enteritidis* that cause infections in chickens are resistant to known antimicrobial agents such as tetracycline, nalidixic acid, ampicillin, and others (see Ribeiro, A. R., Kellermann, A., Santos, L. R., Nascimento V. P. 2008. Resistência antimicrobiana em *Salmonella enteritidis* isoladas de amostras clínicas e ambientais de frangos de corte e matrizes pesadas. *Arq. Bras. Med. Vet. Zootec.* 60 (5): 1259-1262). Such conventional antibiotics are also used for the treatment of human infections. This overlay leads to the emergence of a large increase of resistant strains, which complicates the treatment of infections in humans. Thus, the isolation of new chemical entities with antimicrobial activity for exclusive use in animals will provide significant benefits in raising animals for slaughter, said entities being used as growth promoters and in the treatment of veterinary infections, and these benefits will result not only in increased earnings for producers, but also in the exclusion of the use of current antibiotics in animals consumed by men.

The emergence of resistant bacteria occurred soon after the clinical use of antimicrobial agents like penicillin Since then it became clear that for each new antimicrobial agent that is available on the market a bacteria resistant to these new agents quickly appears, and the rapidity with which this resistance is developed is proportional to the size of the use of new drugs. Recently it was found that the use of antimicrobials in animals used to feed men has caused the emergence of pathogenic bacteria resistant to the antibiotics used to treat infections in humans (for more details, see Wegener H. C. et al. "Public Health Impacts of the Use of Antimicrobials in Food Animals", Proceedings of the WBC Congress, 23rd World Buiatrics Congress, Quebec City, Canada, 2004).

The antimicrobial agents can be natural or synthetic substances which inhibit or kill microorganisms, including bacteria. Currently there are over 15 different classes of antimicrobial substances, which differ in chemical structure and mechanism of action, causing them to be highly specific in the treatment of specific pathogens. The emergence of antimicrobial agents was the great victory of the 20th century in the fields of medicine, veterinary medicine and agriculture, not only for its therapeutic value, but also for its property to promote the growth of plants and animals when used in sub-therapeutic amounts (see "Use of antimicrobials outside human medicine and resultant antimicrobial resistance in humans", Fact sheet No. 268, 01/2002, available on the Web at http://www.who.int/mediacentre/factsheets/fs268/en/).

The problems of the use of antibiotics as antimicrobial agents for the treatment of humans and animals have assumed such a strong position that governmental authorities of different countries have not only promoted researches to minimize the impact of resistance of pathogenic bacteria to existing antibiotics, but also worked in campaigns to educate the public to the increasing risks of this increase in resistance, aiming at reducing the use of antibiotics in animals, especially in subtherapeutic quantities to promote animal growth and improve the yield of meat production. Examples of these government initiatives are: (1) the Report "Overarching AMR" in the UK, published in 2004 (see "Overview of Antimicrobial Usage and Bacterial Resistance in Selected Human and Animal Pathogens in the UK:2004", available on the Web at http://www.dardni.gov.uk/index/publications/pubs-dard-animal-health/pubs-vet-meds.htm) and (2) the work performed by San Martin, B. et al. Funded by the Chilean National Fund for Scientific and Technological Development (see San Martín, B. et al. "Evaluation of Antimicrobial Resistance Using Indicator Bacteria Isolated from Pigs and Poultry in Chile", Intern J Appl Res Vet Med, Vol. 3, No. 2, 171-178, 2005).

One of the most promising paths in the quest to achieve this goal is to use a biological material that is effective as an antimicrobial agent and as a growth promoter in animals, especially in chickens and pigs. In 2004 the group of Dal-Soo identified (see Dal-Soo, K. et al. "*Paenibacillus elgii* sp. nov., with broad antimicrobial activity", International Journal of Systematic and Evolutionary Microbiology 54, 2031-2035, 2004), two strains (SD17 and SD18) which were classified as a new spore-forming bacteria with broad antimicrobial activity, said strains being isolated from roots of *Perilla frutescens*. Later, Dal-Soo, K. ela al. (see Dal-Soo, K. et al. "*Paenibacillus elgii* SD17 as a Biocontrol Agent Against Soil-borne Turf Diseases", Plant Pathol. J. 21(4): 328-333, 2005) identified in strain SD17 a broad-spectrum antimicrobial activity against diseases caused by microorganisms in grass. Laboratory tests conducted with a granule formulation prepared with the fermentation broth of *Paenibacillus elgii* SD17 showed efficacy similar to the commercial fungicides, while field tests with the same formulation showed an efficacy lower than the commercial fungicides. Despite these results on the field, the authors considered the granule formulation made with *Paenibacillus elgii* SD17 an appropriate biocontrol agent.

The search for antimicrobial agents for the treatment of plant diseases caused by microorganisms also resulted in the composition disclosed in WO 09045023, which composition is based on the use of superabsorbent polymers as a support for (a) beneficial microorganisms which inhibit the growth of pathogens in plants and (b) a nutrient medium for said beneficial microorganism. On page 13, line 2 of document WO09045023 *Paenibacillus elgii* SD17 is mentioned as one of the beneficial microorganisms.

EP 1788074 describes new strains belonging to the genus *Paenibacillus* and their use, or the culture of these new strains to control plant diseases. These new strains are *Paenibacillus* sp. BS-0048, *Paenibacillus* sp. BS-0074, *Paenibacillus polymyxa* BS-0105 and *Paenibacillus* sp. BS-0277. This document describes formulations comprising the crude fermentation extract using the new strains and/or compounds produced in these fermentations, such compounds called Fusaricidin A, Fusaricidin B, compound 3 and compound 4 with their chemical formulas defined in claim 3.

As can be seen in the prior art mentioned above there is no mention of the isolation of proteins or peptides with protective activity and promotes of plant growth obtained from *Paenibacillus* sp. And also, there is no report about getting a protein or a peptide derived from *Paenibacillus* sp. with antimicrobial activity and/or growth promoter in animals intended for slaughter for human consumption. Such proteins or peptides bring an important advance in the search for alternatives to reduce the increasing resistance of pathogenic bacteria to antibiotics in use for the treatment of microbial infections in humans.

SUMMARY OF THE INVENTION

The present invention aims at providing *Paenibacillus* sp extract with antimicrobial activity and/or growth promoter in animals intended for slaughter for human consumption comprising new lipopeptides not described in the prior art with antimicrobial activity. More specifically, the invention provides new peptides derived from the fractions of the fermentation of *Paenibacillus* extract, preferably *Paenibacillus elgii*, said novel peptides having antimicrobial activity and promoting the growth of organisms, such as plants and animals. The invention is also related to the use of the extract as a growth promoter and as an antimicrobial agent in the treatment and prophylaxis of animals intended for human consumption.

In an initial embodiment, the present invention comprises a method of preparing an extract containing lipopeptides, the method comprising fermenting *Paenibacillus* and extracting at least one of the following compounds:

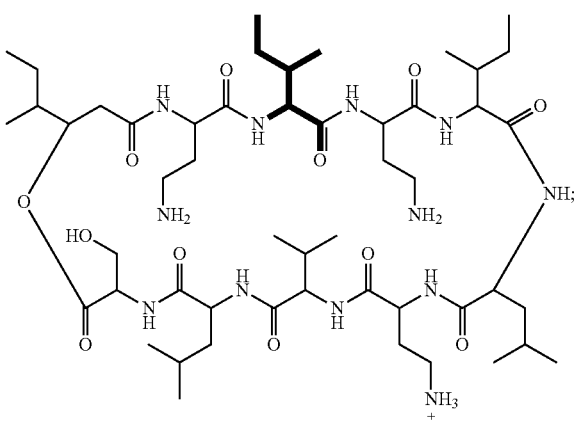

Compound 1

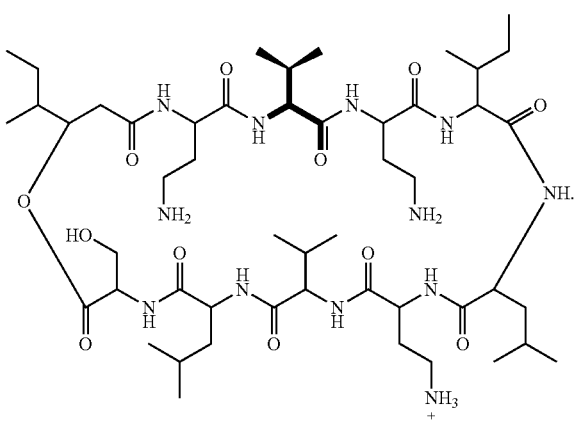

Compound 2

The *Paenibacillus* may be, for example, *Paenibacillus elgii*, *Paenibacillus elgii ourofinensis* or mixtures thereof. The extraction of the lipopeptide may take place by an organic extraction such as a butanol extraction. The process may comprise the step of performing the technique of extracting the *Paenibacillus* extract from the fermentation broth.

In a second embodiment, the present invention comprises a lipoprotein isolated from *Paenibacillus* by n-butanol extraction, the lipoprotein comprising at least one of the following compounds:

Compound 1

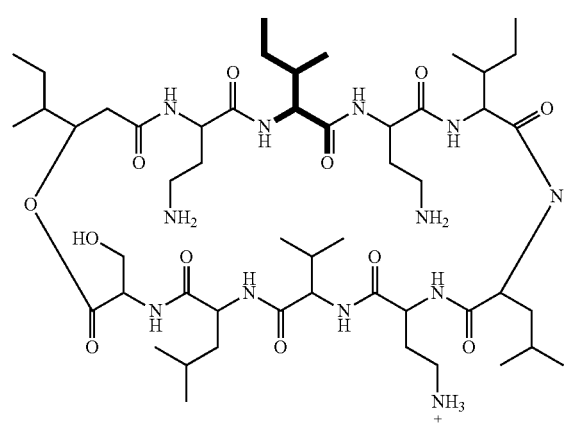

Compound 2

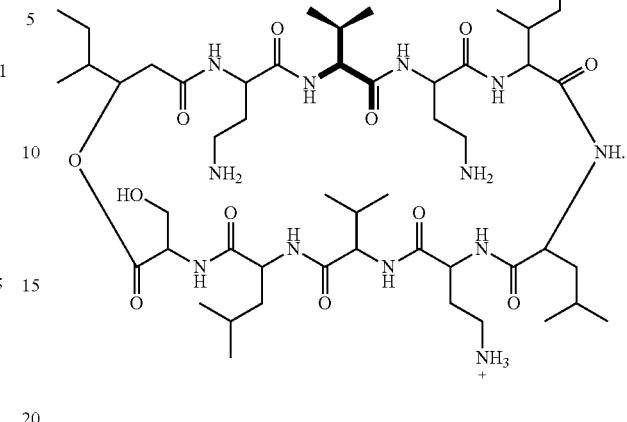

A third embodiment of the invention relates to a method of producing a bacterial extract of *Paenibacillus*, the bacterial extract comprising at least one of the compounds represented below:

Compound 1

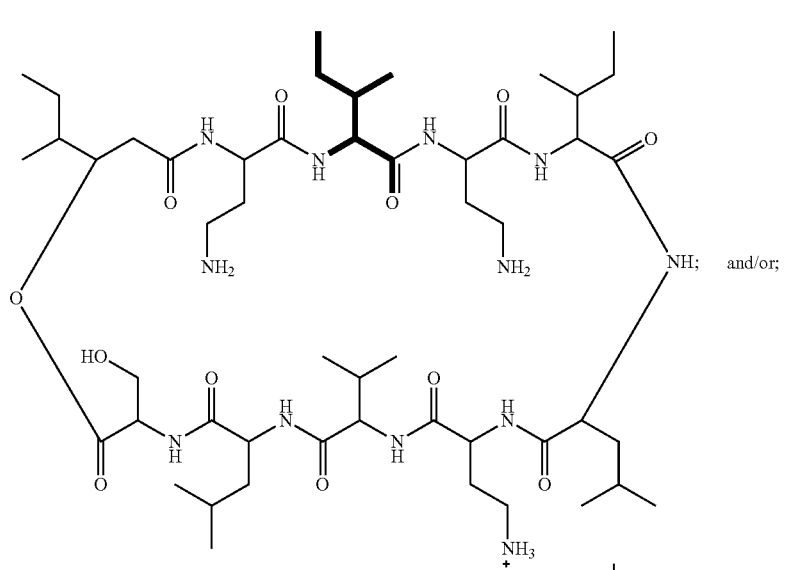

and/ the method comprising performing a n-butanol extraction on a *Paenibacillus* sample or extract thereof.

A fourth embodiment of the invention relates to a method for the prophylaxis and/or treatment of animals or plants, the method comprising administering at least one lipopeptide selected from the group consisting of the following compounds:

Compound 1

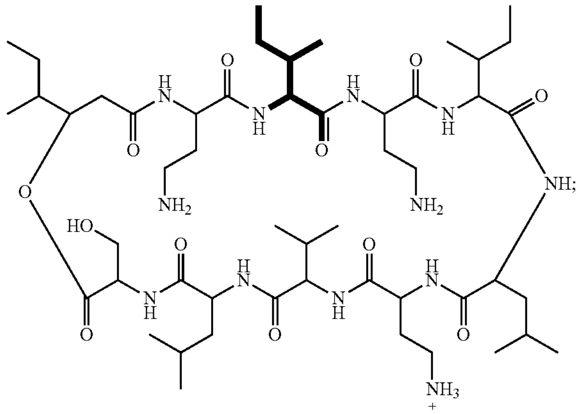

Compound 2

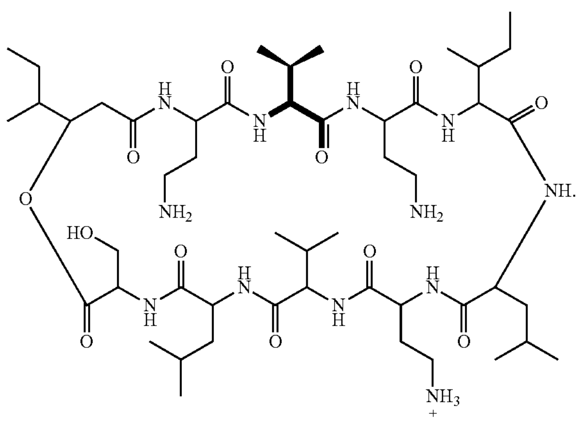

When the method involves the treatment and/or prophylaxis of infections caused by phytopathogens in plants, the extract may optionally be further combined with an agriculturally acceptable carrier or substrate. When the method concerns the treatment and/or prophylaxis of infections in animals, the extract may optionally be further combined with a therapeutic adjuvant, and optionally in addition or in the alternative, a pharmaceutically acceptable carrier or excipient. In one particular embodiment of this method, the lipoprotein may be provided as a component of an animal feed.

A fifth embodiment of the invention relates to a drug composition for the prophylaxis and treatment of animals comprising: (i) a therapeutically effective amount of the culture extract of *Paenibacillus* comprising at least one of the following compounds:

Compound 1

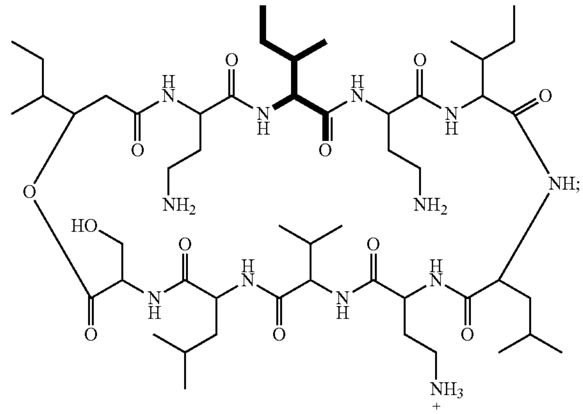

Compound 2 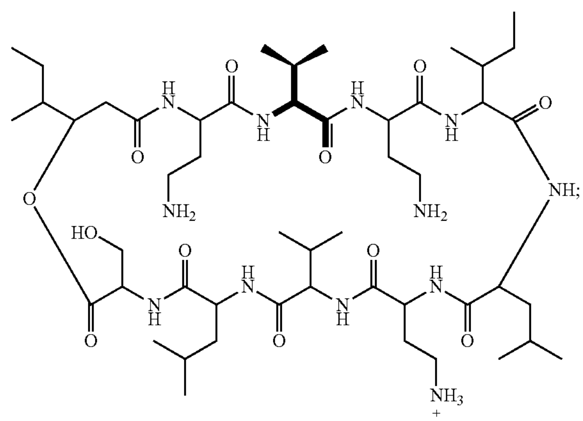 and (ii) a pharmaceutically acceptable carrier or excipient.

A sixth embodiment of the invention relates to a composition for the prophylaxis and treatment of plants comprising: (i) an agriculturally effective amount of at least one of the following compounds:

Compound 1

-continued

Compound 2 and (ii) an agriculturally acceptable carrier or substrate.

A seventh embodiment of the invention relates to the use of the lipopeptides of the present invention as growth promoters and as antimicrobial agents in the treatment or prophylaxis of animals intended for human consumption.

An eighth embodiment of the invention relates to uses of the lipopeptides of the present invention as growth promoters and in the treatment or prophylaxis of the infections caused by phytopathogens in plants.

A ninth embodiment of the invention relates to the use of the extract of the culture of *Paenibacillus* comprising at least one of the following compounds:

Compound 1

Compound 2 as a growth promoter and in the treatment or prophylaxis of conditions involving infections in animals or plants.

DETAILED DESCRIPTION OF THE INVENTION

Figure 1:
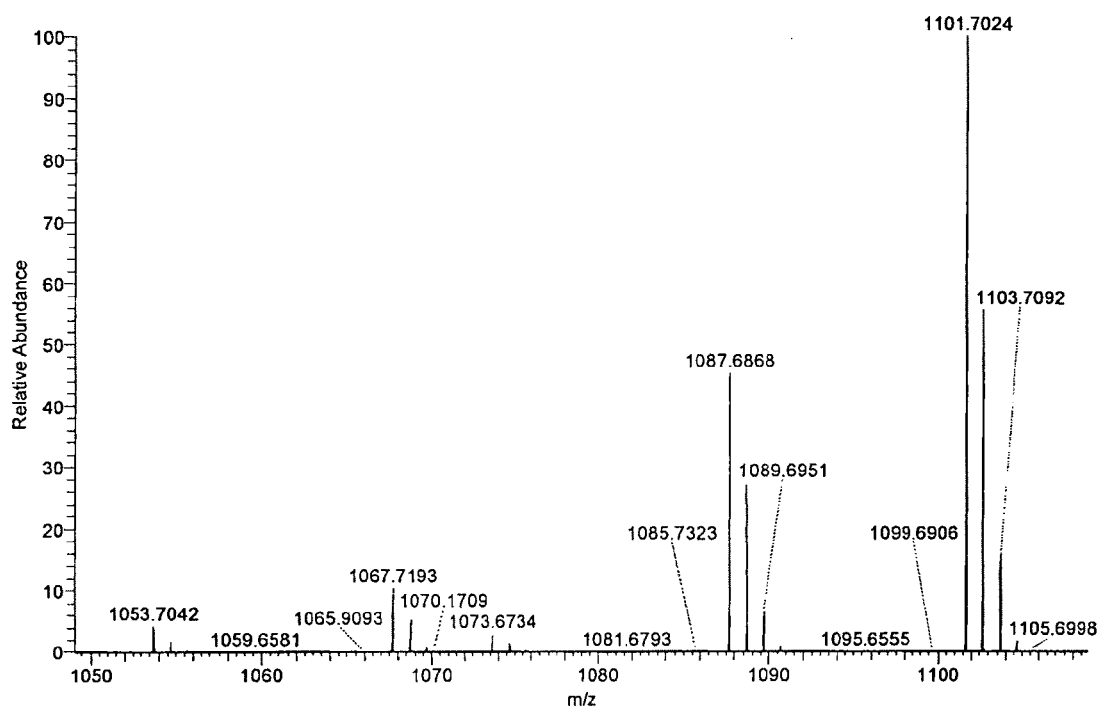
FIG. 1 depicts the FT-MS spectrum of the crude extract produced by *P. elgii*.

To make the understanding of the invention more clear and complete, the terms used in this description are defined as follows:

"antimicrobial"—a term which means extract and peptides originating from *Paenibacillus*, preferably *Paenibacillus elgii*, more preferably *Paenibacillus elgii ourofinensis* that inhibit, prevent or destroy the growth or proliferation of microbes such as bacteria, fungi, protozoa or similar bodies.

"growth promoter"—non-nutrient substances originating from *Paenibacillus* that, when administered to plants by foliar or soil application, or to animals for human consumption orally (for example, incorporated in the feed or water) or by parenteral route, increase the productivity: (a) in the plants through the root vertical growth, extension of leaves, earlier flowering, increased fruit; (b) in the animals, through increased body weight gain, increased feed efficiency, decreased time required for the animal to reach the ideal weight for slaughter, improvement in organoleptic qualities and decreased fat, prevention of infectious or parasitic diseases and decreased mortality.

"therapeutically effective amount"—the term means an amount of antimicrobial agent that is sufficient to effectively inhibit or prevent the establishment, growth or spread of an infection caused by microorganisms sensitive to the peptides or the *Paenibacillus* extract of the invention; or an amount of the growth promoter agent of bodies which is sufficient to effectively promote the growth and development of these organisms, such as animals and plants.

"plant pathogen"—a term that means any and every organism that can cause damage and/or illness to plants and includes fungi, prokaryotes (bacteria and mycoplasma), nematodes, protozoa and similar bodies.

"adjuvant therapy"—a term that corresponds to the agents that aid or increase the action of the active ingredient, or that affect the absorption, the mechanism of action, the metabolism or elimination of the active ingredient in order to increase its effects, in order to fight an infection caused by microbes, that is, the process of growth of organisms such as plants and animals; additionally, this term includes prophylactic activity in the elevation of the immune response developed by the peptides or the *Paenibacillus* extract of the invention.

"additive"—a term that means substances added to the composition for the treatment of plants in order to increase efficiency or modify certain properties of the formulation, such as the absorption of the active ingredient, aiming at facilitating the application or minimizing certain problems.

"pharmaceutically acceptable vehicle or excipient"—a term that means, in a drug composition for therapeutic or prophylactic activity, any and every substance that, at the concentrations present in the dosage form, does not have pharmacological activity, being employed in the composition in order to provide the dosage form with characteristics which ensure its stability, bioavailability, acceptability and ease of administration or application, and which works as carrier of the active ingredient with antimicrobial and/or growth promoter activity of the target animal.

"agriculturally acceptable carrier or substrate"—a term that means, in a composition for the treatment of plants, any and every substance that has no therapeutic or prophylactic action and serves as a carrier of the active ingredient with antimicrobial and/or growth promoter action of the target plant.

In the sequences described herein, nucleotides should be understood to be represented by their standard one letter abbreviations: A for adenine, G for guanine, C for cytosine, T for thymine and U for uracil. The presence of a mixture of nucleotides may also be indicated with an abbreviation as recognized in the art: N for any base (A, C, G or T/U), R for purine (G or A), Y for pyrimidine (T/U or C), M for amino (A or C), K for keto (G or T/U), S for G or C, W for A or T/U, V for nucleotides other than T (A, C, or G), D for nucleotides other than C (A, G, or T), B for nucleotides other than A (C, G, or T), and H for nucleotides other than G (A, C, or T).

The invention provides new agents with antimicrobial and growth promoter activity of organisms from the identification and isolation of these new agents of *Paenibacillus*. The identification of these agents led to obtaining the extract of the fermentation broth and the preparation of peptides with antimicrobial activity and growth promoter of animals and plants. The importance of this preparation lies in the fact that it permits the use of said extract and peptides, among others, to control bacteria and fungi that cause loss in raising of economically important animals (e.g., chickens and pigs). In addition to this antimicrobial activity, said extract and peptides also act as growth promoters of plants and as inhibitors of plant infection by phytopathogens.

First, the invention is based on the process of obtaining, isolating and identifying new lipopeptide found in bacterial isolate extracts. These new bacterial compounds are capable of producing antimicrobial activity against numerous bacteria and fungi which cause veterinary infections, these strains already being resistant to the current antibiotics. Specifically, this invention provides, in one of its embodiments, the use of supernatant and/or extract of the culture comprising new lipopeptide found in bacterial isolate extracts to control veterinary infections and promote the growth of animals.

The invention also provides a method of cultivating a *P. elgii ourofinensis* strain capable of producing the antimicrobial compounds, compounds 1 and 2. The *P. elgii ourofinensis* was submitted to an adaptation step under non-natural conditions wherein the strains were incubated with several mediums and substrates. Samples of the *P. elgii ourofinensis* were extracted with n-butanol/ethyl acetate (8:2) and analyzed by mass spectrometry in positive mode and SIR acquisition mode to verify the presence of the compounds permetin A (m/z 1102), permetin 2 val (m/z 1088) and compounds 1 and 2 (m/z 1068 and m/z 1054). The antimicrobial activity of the samples were also verified in Agar TSA plates comprising *S. epidermidis* indicator microorganism.

It has been found that *P. elgii ourofinensis* adapted by cultivation in Farmal medium (corn steep liquor) showed the presence of compound 1 and 2, significant antimicrobial activity, improved yields, and lower costs compared to the other tested culture media. In one example, the *P. elgii ourofinensis* is cultivated in 2% Farmal medium at pH 7.0 for at least 5 hours, such as from 5 to 8 hours.

As it will be detailed later, after electrophoretic and chromatographic analyzes of the lyophilized sample of the fermentation broth of the new isolate, the separation process provided moieties which were analyzed, and at least two of the lipopeptides responsible for the antimicrobial activity were identified. This identification was performed by sequencing, and the results of this analysis demonstrated that there is no other sequence similar to the ones of the present invention in the databases of proteins and peptides, indicating that new lipopeptides with antimicrobial activity were isolated.

The present invention relates in a first embodiment to the process of obtaining a new bacterial extract having at least one biological activity among antimicrobial activity with respect to microorganisms that cause disease or damage in animals and plants and activity growth promoter of said animals and plants, said new bacterial extract being characterized in that it comprises at least one of the new compounds described below:

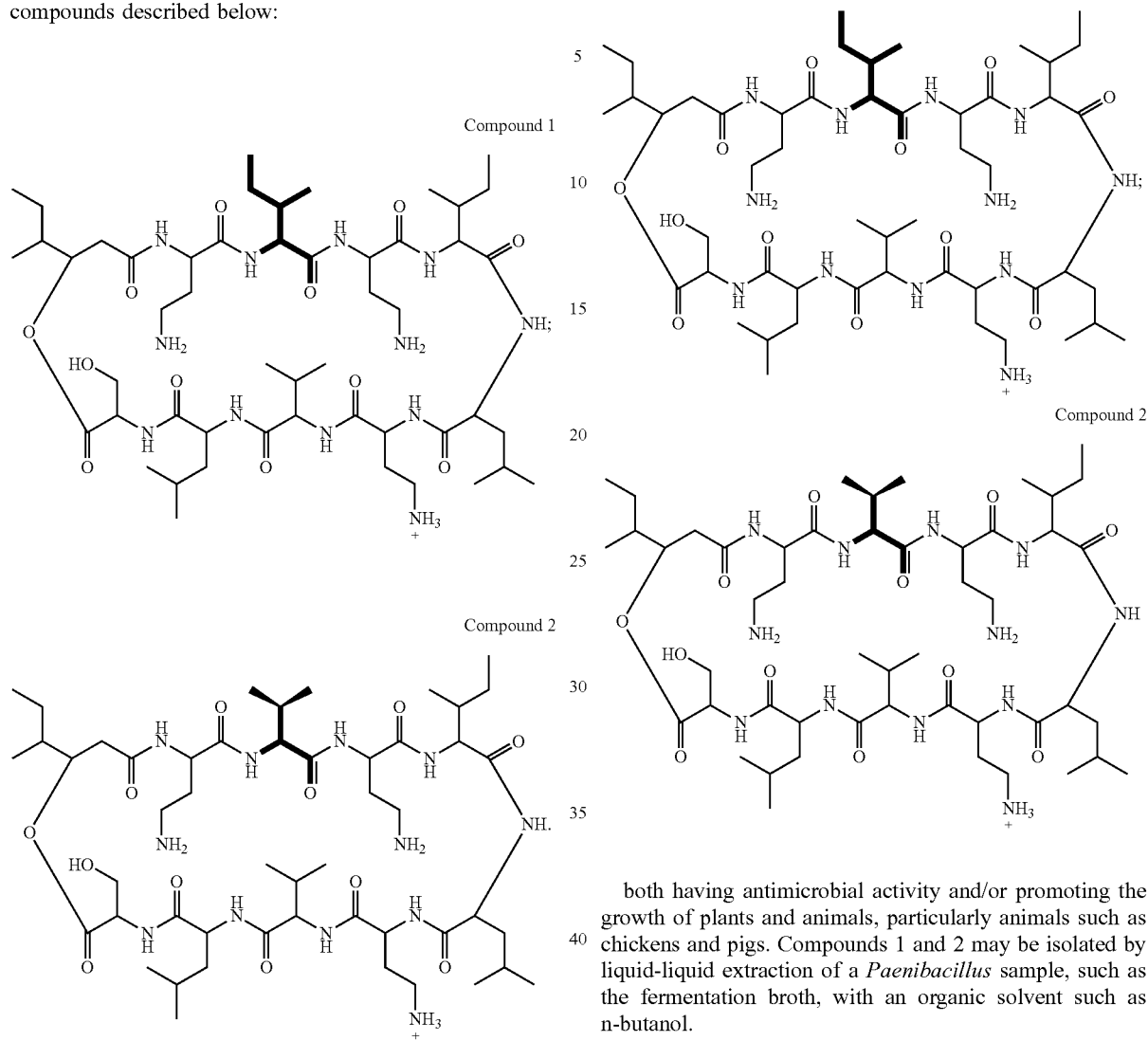

The terms "compound" and "lipoprotein" are used interchangeably in the present invention to refer to the new chemical elements found in the extract from *Paenibacillus*, in the extract, for example, from *Paenibacillus elgii* or in the extract from *Paenibacillus elgii ourofinensis*.

The term "bacterial extract" is intended to mean, in this description, the extract obtained from processing *Paenibacillus*, preferably from fermented *Paenibacillus*. In a particular embodiment, the processing of fermented *Paenibacillus* for the extraction is carried out by methods known in the art such as, for example, liquid-liquid extraction of fermentation broth using an organic solvent such as, but not limited to, n-butanol, or by extraction with ion-exchange cartridge.

The present invention also relates to specific lipopeptides comprising compounds 1 and/or 2 described below, and a method for producing the same:

both having antimicrobial activity and/or promoting the growth of plants and animals, particularly animals such as chickens and pigs. Compounds 1 and 2 may be isolated by liquid-liquid extraction of a *Paenibacillus* sample, such as the fermentation broth, with an organic solvent such as n-butanol.

The lipopeptides of the present invention may be produced by known techniques and obtained in a substantially pure form. For example, lipopeptides can be synthesized manually or in an automated synthesizer, or they may be isolated from the fermentation broth of bacteria *Paenibacillus*. Additional advantages may be provided by the present invention including a method of cultivation of *Paenibacillus*, including *P. elgii*. In one example, *P. elgii ourofinensis* is cultivated in 2% Farmal medium (Farmal HWS3741 from Corn Products Brazil, containing 9.83% of Alanine; 3.68% of Arginine; 5.82% of Aspartic Acid; 2.20% of Cysteine; 18.07% of Glutamic Acid; 5.27% of Glycine; 3.72% of Histidine; 3.07% of Isoleucine; 8.28% of Leucine; 4.75% of Lysine; 3.09% of Tyrosine; 1.98% of Methionine; 2.85% of Phenylalanine; 9.64% of Proline; 5.18% of Serine; 4.08% of Threonine; 5.16% of Valine; 0.3 mg/Kg of Biotin; 3,500.0 mg/Kg of Choline; 6,000.0 mg/Kg of Inositol; 80.0 mg/Kg of Niacin; 15.0 mg/Kg of Pantothenic Acid; 9.0 mg/Kg of Pyridoxine; 6.0 mg/Kg of Riboflavin; 3.0 mg/Kg of Thiamine; 0.14% of Calcium; 0.6% of Magnesium; 2.8% of Potassium; 0.1% of Sodium; 1.8% of Phosphorus; 0.6% of Sulfur; 15.0 mg/Kg of Copper; 20.0 mg/Kg of Manganese; 100.0 mg/Kg of Iron; 0.3 mg/Kg of Selenium; 60.0 mg/Kg of Zinc; the Tryptophan content is destroyed during acid hydrolysis) at pH 7.0 for at least 5 hours, such as from 5 to 8 hours. Other concentrations of Farmal medium may also be used, including 5% and 10% for example, as may other incubation times such as approximately 24 or 48 hours or more.

The present invention also relates to drug compositions for the treatment and prophylaxis of animals for animals intended for human consumption, said compositions comprising: (i) a therapeutically effective amount of at least one of the compounds of the present invention; and (ii) a pharmaceutically acceptable carrier or excipient; and (iii) optionally, a therapeutic adjuvant. As mentioned before, the lipopeptides of the invention have antimicrobial activity and/or activity growth promoter of said animals.

The invention also relates to a method for the treatment and/or prophylaxis of animals intended for human consumption or of plants. The method comprises administering a lipopeptide selected from the group consisting of:

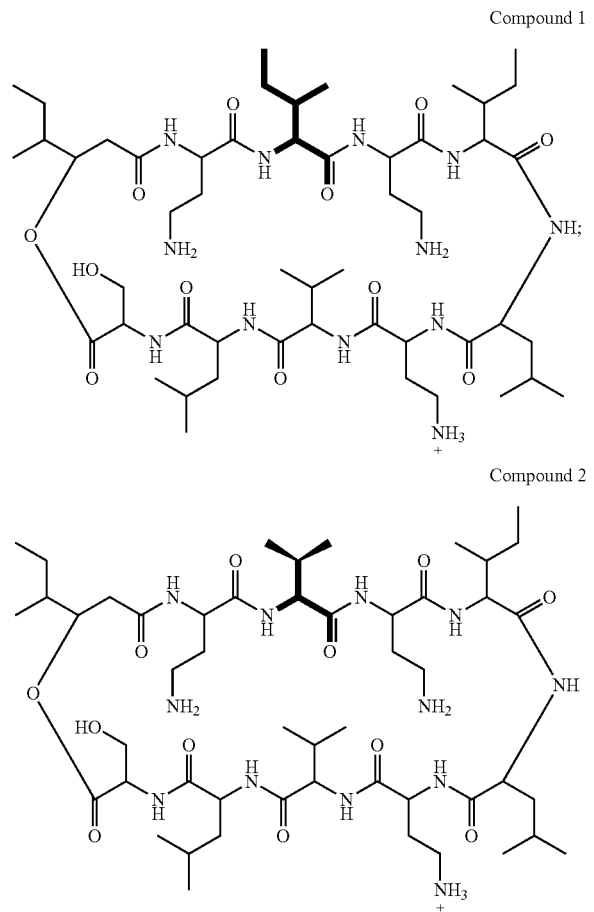

And mixtures thereof. For the treatment and/or prophylaxis of animals the method may include administration of (i) a therapeutically effective amount of the culture extract of *Paenibacillus* having at least one of the compounds of the present invention; (ii) optionally, a pharmaceutically acceptable carrier or excipient; (iii) in addition or in the alternative, optionally, a therapeutic adjuvant. Said extract can be in the liquid form, corresponding to the liquid phase (supernatant) separated from the fermentation broth, or it may be in the dry state after drying, for example, by lyophilization of said liquid phase. Also optionally, the lipopeptide may be provided as a component of an animal feed.

The drug compositions of the invention contain as active ingredient at least one of the lipopeptides of the present invention, or mixtures thereof, in combination with a pharmaceutically acceptable carrier or diluent, and optionally one or more therapeutic adjuvants. Therefore, the active ingredients according to the invention can be administered individually or together in any conventional dosage/veterinary form of oral or parenteral administration. For oral administration, the composition of the invention may be in the form of a solution, suspension, tablet, pill, capsule, powder, and the solid forms can be of quick release, controlled release or delayed release, or any combination of these types, and said forms may be added to the water or feed of animals.

The tablet form contains various excipients such as sodium citrate, calcium carbonate, calcium phosphate and the like, along with disintegrants such as starch or complex silicates. It is also common the use of binding agents in this dosage form such as polyvinylpyrrolidone, sucrose, gelatin and acacia, and additionally lubricating agents such as magnesium stearate, sodium lauryl sulfate and acacia.

Other appropriate solid dosage/veterinary forms include powders which can be either water dispersible or they may be enclosed in gelatin capsules as hard-type capsules or soft-type capsules. In this case, the excipient includes lactose or polyethylene glycols of varying molecular weights.

In the case of liquid dosage forms for oral administration, sweeteners, flavoring agents, dyes, emulsifying agents or suspending enhancers and diluents may be used in the excipient, such as water, ethanol, propylene glycol, glycerin and combinations thereof.

The pharmaceutical compositions containing the active ingredients of the invention are usually prepared following conventional methods, and are administered in the appropriate dosage/veterinary form.

As an example, the oral solid dosage/veterinary forms may contain, along with the active ingredient, diluents, lubricants, binders, disintegrating agents and others. Examples of diluents that may be used in the pharmaceutical/veterinary compositions of the invention are: lactose, dextrose, saccharose, cellulose, corn starch or potato starch. Examples of lubricants that may be used in the pharmaceutical/veterinary compositions of the invention are: silica, talc, stearic acid, magnesium or calcium stearate and/or polyethylene glycols. Examples of binding agents that may be used in the pharmaceutical/veterinary compositions of the invention are: starches, arabic gum, gelatin, methylcellulose, carboxymethylcellulose or polyvinyl pyrrolidone. Examples of disaggregating agents that may be used in the pharmaceutical/veterinary compositions of the invention are: starch, alginic acid, starch or sodium alginates or glycolates; effervescent mixtures; dyes; sweeteners. Additionally, the pharmaceutical/veterinary compositions of the invention can use wetting agents such as lectin, polysorbates, laurylsulphates, and in general, pharmacologically inactive and non-toxic substances commonly used in pharmaceutical/veterinary formulations. The preparation of said pharmaceutical/veterinary compositions of the invention can be carried out in a known manner, for example by means of mixing, granulating, pressing into tablets, sugar-coating, or film-coating processes. The liquid dispersions for oral administration may be e.g. syrups, emulsions and suspensions. In addition to the active ingredient of the present invention, the syrups may contain one or more carrier agents, for example, saccharose or saccharose with glycerine and/or mannitol and/or sorbitol. The suspensions and the emulsions may contain as carrier, for example, a natural gum, agar, sodium alginate, pectin, methylcellulose, carboxymethylcellulose or polyvinyl alcohol. For parenteral administration, it is conventional to use sterile, pharmaceutically acceptable oils, and propylene glycol may also be employed, as well as sterile aqueous solutions.

The drug compositions of the present invention may also contain one or more therapeutic adjuvants. Examples of such adjuvants are: phosphatide-polysaccharide conjugate as described in U.S. Pat. No. 5,785,975; Veterinary emulsion-based adjuvants, e.g. Emulsigen® (MVP Technologies, Omaha, Nebr.), Carbigen™ (MVP Technologies, Omaha, Nebr.), Polygen® (BASF Aktiengesellschaft, Germany); adjuvants such as the acrylic polymer and the dimethyl dioctadecyl ammonium bromide, disclosed in US2009/0017067; sub-micron oil-in-water squalene emulsion, polyoxyethylene, sorbitan monooleate and sorbitan trioleate, known by the brand name MF59™ (Novartis AG, Basel, Switzerland), and other examples may also be mentioned.

Additionally, the invention also relates to a composition for the prophylaxis and treatment of plants comprising: (i) a therapeutically effective amount of at least one of the lipopeptides of the present invention; (ii) an agriculturally acceptable carrier or substrate; and (iii) optionally, at least one additive.

In another embodiment of the invention, said composition for the treatment and prophylaxis of plants comprises: (i) an agriculturally effective amount of the culture extract of *Paenibacillus* comprising the lipopeptide of the present invention; (ii) an agriculturally acceptable carrier or substrate; and (iii) optionally, at least one additive.

The formulation of the invention may be in liquid or solid form, for example in the form of a wettable powder. Both formulations, dry or liquid, shall be packed in containers and in conditions that preserve the integrity of the active ingredients. Liquid formulations have lower shelf life, but the dry formulations (e.g., wettable powder) require less stringent conditions, such as storage in a cool place in the absence of light and moisture, and the product may be stored from one crop to another, since packed in freezer or refrigerator.

The formulations of the invention generally contain an amount of active ingredient effective to control microorganisms harmful to plants and/or promote plant growth, said active ingredient comprising the lipopeptides of the present invention described below:

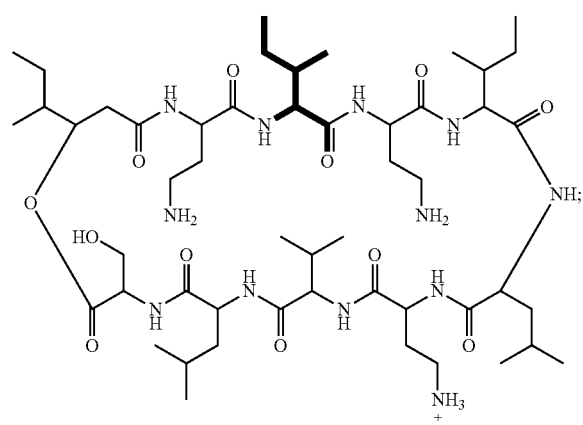

Compound 1

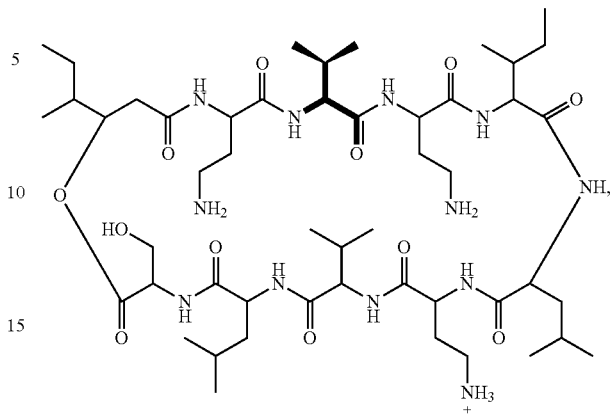

Compound 2 or mixtures thereof, in combination with an agriculturally acceptable carrier in the form of a solid or liquid diluent, preferably solid. Formulations that may be used include powders, granules, pellets, suspensions, emulsions, wettable powders, flowable solids, and the like, provided that such forms are consistent with the physical chemical properties of the active ingredient and compatible with the lipopeptides of the present invention, with the mode of application and environmental factors such as soil type, humidity and temperature. Formulations in spray may also be used, especially when the application areas are large. The more concentrated compositions are also within the scope of protection of the present invention, and said compositions are suitable for use as intermediates to the diluted final product to be applied.

The formulations of the invention will typically contain effective amounts of the active ingredient, one or more diluents, one or more surfactants and other appropriate additives to obtain the desired product characteristics. Furthermore, it should be clear that the active ingredient used in the present invention can also be used alone in special applications where a high concentration of the composition of the invention is required.

Other formulating agents present in minor amounts can be added to the compositions of the invention such as additives to reduce foaming, clumps, corrosion, unwanted microbial growth, and other similar agents. Another essential feature of the formulation of the present invention is the need for ensuring that all ingredients of the composition are mutually compatible and do not contribute to loss of antimicrobial and/or growth promoter activity characteristic of the active ingredient of the invention.

The compositions of the present invention can also be mixed with other agricultural chemicals, fertilizers, soil conditioners, stabilizers, or with one or more insecticides, fungicides, acaricides, or other biologically active compounds to form a multicomponent formulation. Examples of other protection products in agriculture as the active ingredient of the formulation of the present invention that may be mixed are insecticide-type sodium channel agonist (e.g., pyrethroid), sodium channel blocking agents (for example, pyrazolines), acetylcholinesterase inhibitors (e.g., organophosphates and carbamates), nicotinic acetylcholine binding agents, gabaergic binders, agonists or antagonists of octapine (e.g., formamidine) insecticides from the pyrrole group and others.

Below is presented by way of example the isolation of the compounds comprised in the *Paenibacillus* extract. Among these are described and characterized the new and inventive compounds of the present invention. However, it should be understood that this example is provided for illustrative purposes only and that various modifications or changes in light of the embodiments disclosed herein are suggestive to those skilled in the art and are to be included within the spirit and scope of this disclosure and the scope of the accompanying claims.

Example 1

The organic extract obtained by liquid-liquid extraction of *Paenibacillus elgii* fermentation broth in n-butanol shows a mixture of 5 lipopeptides belonging to the class of Permetinas. Among these, compounds of m/z 1067.7 and 1053.7 are unpublished. The signal of m/z 1101.7 was assigned to the presence of permetina A, the signal of m/z 1087.7 was assigned to the presence of compound BMY-28160, and the signal of m/z 1073.7 was assigned to the compound Pelgipeptin A. These compounds were characterized by ultra resolution mass spectrometry using a spectrometer FT-ICR-MS and collision-induced dissociation experiments (CID). These two experiments confirm the proposed structure for all lipopeptides present in the organic extract produced by *Paenibacillus elgii*, as detailed below.

Structural Characterization of Lipopeptides Produced by *Paenibacillus elgii*.

The organic extract obtained by liquid-liquid extraction of fermentation broth of *Paenibacillus elgii* in n-butanol was analyzed by ultrasonic resolution mass spectrometry. The spectrum obtained is shown in FIG. 1.

The signals of m/z observed in the mass spectrum of FIG. 1 were characterized as belonging to the class of Permetinas. Permetinas are lipopeptides containing 9 amino acids linked to a lipid chain of a 6-carbon β-hydroxy acid.

Figure 2:
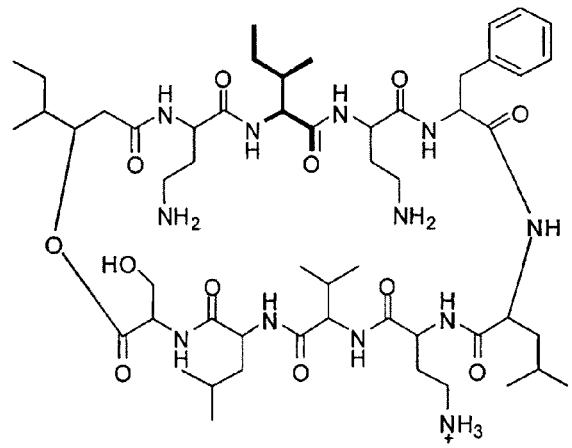
FIG. 2 depicts the formula of Permetina A.

The signal of m/z 1101.7024 was assigned to the presence of Permetina A (FIG. 2). The signal was obtained with a variation of ΔMM=0.5 ppm, which is in accordance with the structural formula proposed for Permetina A.

The signal of m/z 1101.7 was subjected to sequence mass spectrometry experiments (MS/MS) for fragmentation and structural characterization studies. The spectrum of collision-induced fragmentation (ICD) is shown in FIG. 3.

Figure 3:
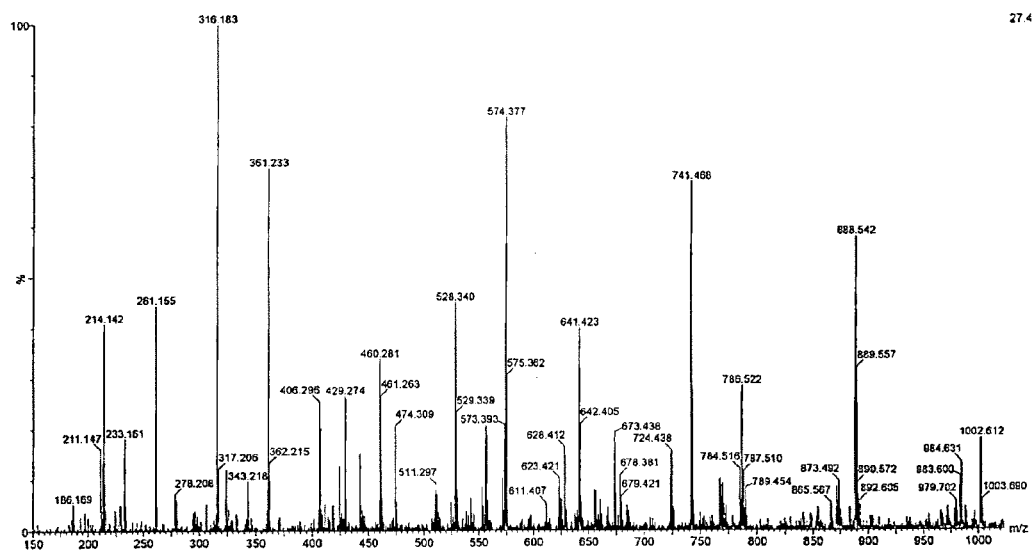
FIG. 3 depicts the spectrum of CID of the ion m/z of 1101.7 of Permetina A.
Figure 4:
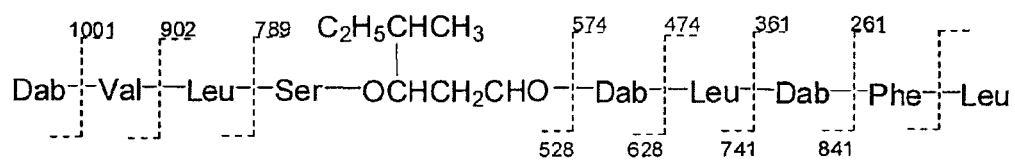
FIG. 4 depicts the proposed cleavage of Permetina A.

The spectrum of MS/MS obtained for the ion of m/z 1101.7 shown in FIG. 3 is identical to the spectrum obtained by Wu and colleagues in the characterization studies of permetina A. The major ion fragments which show the presence of Permetina A are shown in FIG. 4.

Figure 5:
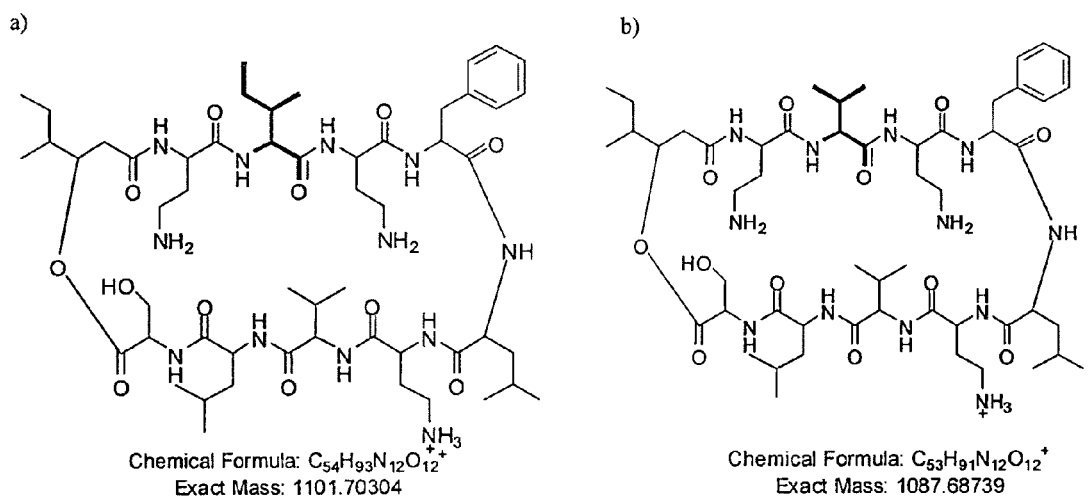
FIG. 5 depicts the structural formula of the lipopeptides a) BMY-28160 and b) Permetina A.

The signal of m/z 1087.6868, which was attributed to the presence of the lipopeptide BMY-28160, is a lipopeptide analogue of Permetina A. In compound BMY-28160 the amino acid at position 2 is Valine (Val), different from Permetina A, where the amino acid in this second position is a Leucine/Isoleucine (Leu/Ile) as shown in FIG. 5.

Signals of m/z 1073.6734, 1067.7193 and 1053.7042 were also observed in the mass spectrum shown in FIG. 1. Wu and colleagues[2] have identified the signal of m/z 1073.6734, which was assigned to a lipopeptide analog of BMY-28160 with a difference of 14 Da, which was assigned as a methylene group (—CH$_2$—).

However, the signs of m/z 1067.7193 and 1053.7042 were first identified in this crude extract, and are considered novel lipopeptides.

Figure 6:
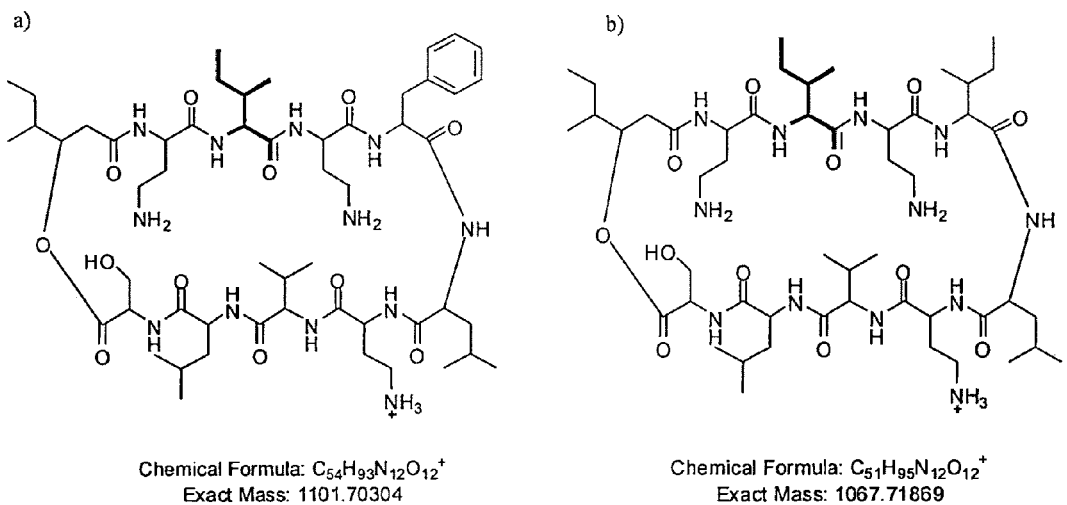
FIG. 6 depicts the structural formula of a) Permetina A and b) novel Compound 1.

The signal of m/z 1067.7193 was attributed to the presence of the lipopeptide analogue of Permetina A (FIG. 6). The signal was obtained with a variation of ΔMM=0.5 ppm, which is in accordance with the molecular formula proposed for Compound 1.

Figure 7:
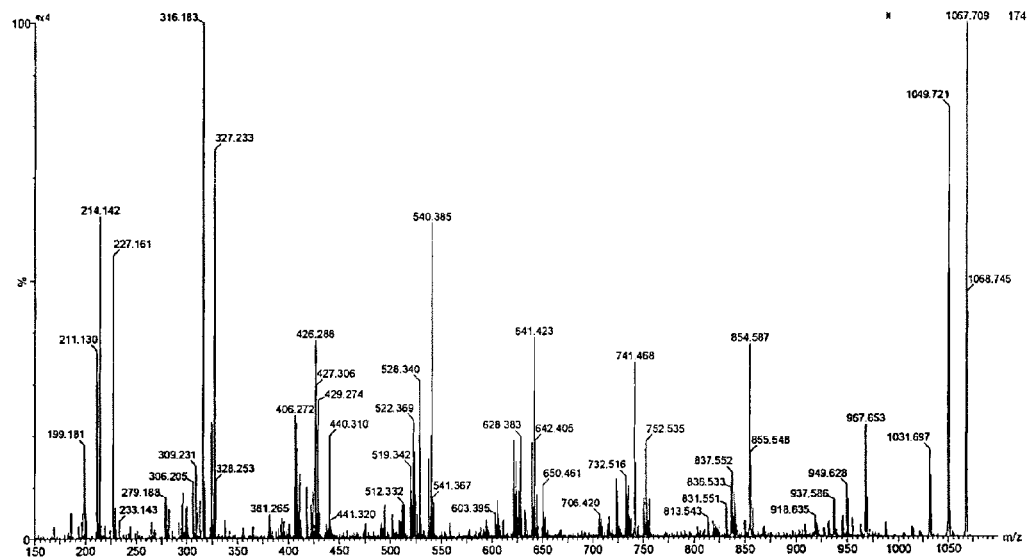
FIG. 7 depicts the spectrum of CID of the ion of m/z 1067.7 of the novel compound 1.

Experiments of MS/MS were performed for the structural characterization and sequencing of the amino acids present in the compound 1. The spectrum obtained in this CID experiment is shown in FIG. 7.

Based on the fragmentation patterns, the amino acid sequence of compound 1 was characterized as an analog of Permetina A in which the amino acid phenylalanine (Phe) in position 4 of Permetina A was replaced by the amino acid leucine/isoleucine (Leu/Ile) in FIG. 6.

Figure 8:
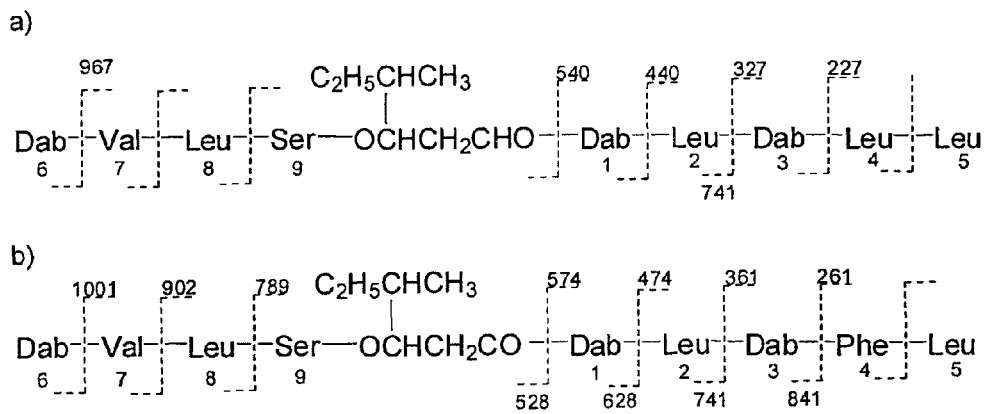
FIG. 8 depicts a comparative study of fragmentation patterns for a) compound 1 and b) Permetina A.

A comparative study of fragmentation patterns for Permetina A and compound 1 is presented in FIG. 8.

The formation of fragment ions of m/z 327 and 440 in the CID spectrum of compound 1 (FIG. 7) confirm the presence of the amino acid leucine/isoleucine at positions 2 and 4.

The signal of m/z 1053.7 observed in the mass spectrum of the crude extract (FIG. 1) was assigned to a second novel compound. This compound was characterized as being a lipopeptide analogue to lipopeptide BMY-28160. The signal was obtained with a variation of ΔMM=1.1 ppm, which is in accordance with the molecular formula proposed for compound 2.

Figure 9:
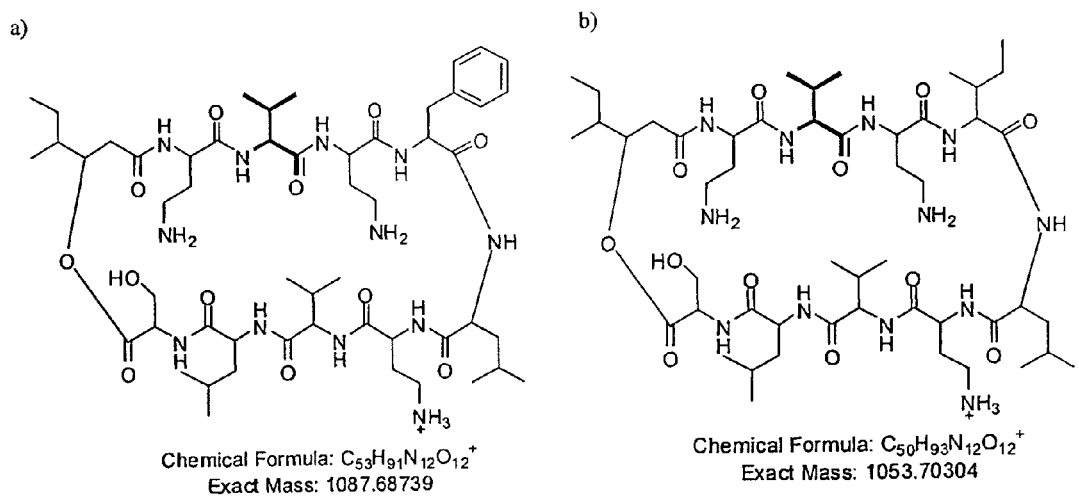
FIG. 9 depicts the molecular formula of the lipopeptides a) BMY-28160 and b) Compound 2.

The structural difference between the two compounds is that for the lipopeptide BMY-28160 the amino acid at position 4 is a Phenylalanine (Phe) and for the novel compound the amino acid at position 4 is a leucine/isoleucine (Leu/Ile) as shown in FIG. 9.

The signal of m/z 1053.7 was subjected to CID experiments with the aim of obtaining information about the amino acid sequencing of this new compound. The fragmentation spectrum obtained is shown in FIG. 10.

Figure 10:
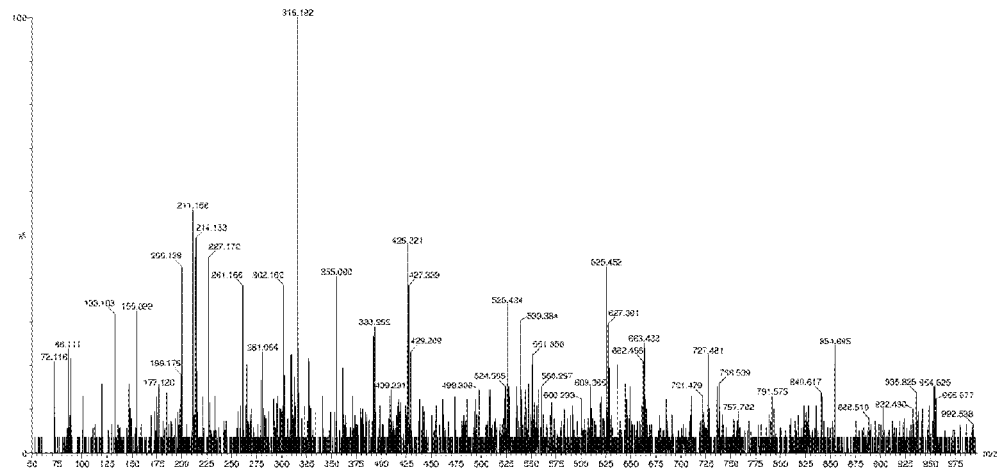
FIG. 10 depicts the spectrum of CID of the ion of m/z 1053.7 corresponding to compound 2.
Figure 11:
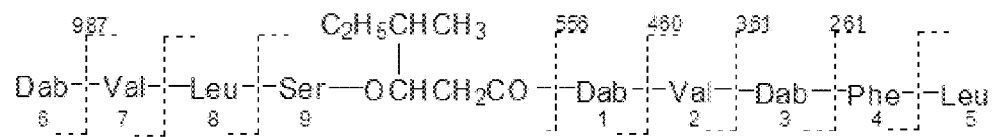
FIG. 11 depicts a comparative study of fragmentation patterns for the lipopeptides a) BMY-28160 and b) compound 2.
Figure 11:
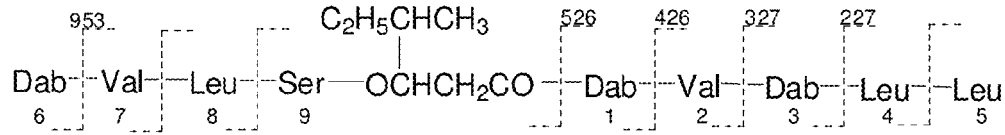

The fragments of ion of m/z 227 and 426 observed in the spectrum of FIG. 10 as well as the comparative study of the fragmentation patterns between lipopeptide BMY-28160 and compound 2 shown in FIG. 11 confirm the structural assignment presented for compound 2 in FIG. 9.

Example 2

Several studies were performed in order to develop a process to cultivate a *P. elgii ourofinensis* strain capable of producing the antimicrobial compounds, Compounds 1 and 2, with significant yield and antimicrobial activities. The strain *P. elgii ourofinensis* was cultivated under non-natural conditions wherein the strains were incubated in several media and substrates. Samples of the *P. elgii ourofinensis* were collected each 12 hours for the first two days of experiment, and each 24 hours for the remaining 13 days.

The samples of fermentation broth were extracted with n-butanol/ethyl acetate (8:2) and analyzed by mass spectrometry in positive mode and SIR acquisition mode to verify the presence of the compounds permetin A (m/z 1102), permetin 2 val (m/z 1088) and compounds 1 and 2 (m/z 1068 e m/z 1054. The antimicrobial activity of the samples were also verified in Agar TSA plates comprising *S. epidermidis* indicator microorganism.

It has been found that the *P. elgii ourofinensis* adapted by growth in Farmal medium (also referred to as corn steep liquor), showed the presence of compound 1 and 2, significant antimicrobial activity during the course of the experiment, improved yields, and lower costs when compared to the other tested culture media. In the examples below, the Farmal medium was made with Farmal HWS3741 from Corn Products Brazil, containing 9.83% of Alanine; 3.68% of Arginine; 5.82% of Aspartic Acid; 2.20% of Cysteine;

18.07% of Glutamic Acid; 5.27% of Glycine; 3.72% of Histidine; 3.07% of Isoleucine; 8.28% of Leucine; 4.75% of Lysine; 3.09% of Tyrosine; 1.98% of Methionine; 2.85% of Phenylalanine; 9.64% of Proline; 5.18% of Serine; 4.08% of Threonine; 5.16% of Valine; 0.3 mg/Kg of Biotin; 3,500.0 mg/Kg of Choline; 6,000.0 mg/Kg of Inositol; 80.0 mg/Kg of Niacin; 15.0 mg/Kg of Pantothenic Acid; 9.0 mg/Kg of Pyridoxine; 6.0 mg/Kg of Riboflavin; 3.0 mg/Kg of Thiamine; 0.14% of Calcium; 0.6% of Magnesium; 2.8% of Potassium; 0.1% of Sodium; 1.8% of Phosphorus; 0.6% of Sulfur; 15.0 mg/Kg of Copper; 20.0 mg/Kg of Manganese; 100.0 mg/Kg of Iron; 0.3 mg/Kg of Selenium; 60.0 mg/Kg of Zinc; the Tryptophan content is destroyed during acid hydrolysis.

In addition, an optimal Farmal concentration to obtain the compounds of the invention was evaluated. Specifically, the *P. elgii ourofinensis* strain was cultivated in Farmal medium at different concentrations, 2%, 5% and 10%. It was expected that the more concentrated medium would lead to higher antimicrobial compounds content. However, it has been found that the Farmal 2% medium showed superior dry weight, 2.24 g/L, while the dry weight of the 5% and 10% Farmal mediums was, respectively, 2.0 g/1 and 2.17 g/L. Further, the time required to reach the end of the fermentation process, when the pH 8.2-8.3 is reached, was significantly lower in the 2% Farmal medium, 21 hours, while 5% and 10% Farmal mediums took, respectively, 31 and 63 hours. This reinforces that the 2% Farmal medium besides providing better yields, also reduces the costs of the process by requiring less processing time and, thus, less manpower, raw material and process expenditures.

A process to obtain the antimicrobial compounds from *P. elgii ourofinensis* strains comprises culturing the *P. elgii* in 2% Farmal medium at pH 7.0, from 5 to 8 hours.

Identification of *P. elgii ourofinensis*
Biochemical Tests

To characterize and identify *P. elgii ourofinensis*, biochemical tests based on metabolic differences between species were performed.

The catalase test was performed adding $H_2O_2$ 30% in the presence of the *Paenibacillus* and *S. epidermidis* isolates as the positive control. The isolate was not able to produce catalase because it did not convert the $H_2O_2$ into oxygen, gas and water. The oxidase test was carried out with filter paper comprising a reducing agent that acts as a final acceptor to the electron from the cytochrome C oxidase. The reducing agent changes its color when it passes from the reduced state to the oxidized state, causing a visual reaction which allows identification of the presence of the enzyme in the bacteria. In addition, *P. aeruginosa* was used as a positive control. The appearance of a pink purple coloring in the *P. ourofinensis* was not noted, while it was very visible in the *P. aeruginosa* control.

The four following tests were carried out with an *E. coli* strain as a positive control. The citrate test was used to verify if the isolate uses citrate as its only carbon source. The SIM agar test (Sulfurindolemotility agar) was used to identify the ability to produce $H_2S$ to observe motility and the indole production detected by addition of Kovac reagent. The TSI agar test (triple sugar iron) was carried out to measure the bacterial ability to use the three sugars: glucose, lactose and sucrose, respectively at, 0.1%, 1.0% and 1.0%. The indole test was carried out to verify the bacteria ability to use the pyruvic acid and ammonia to satisfy its nutritional requirements, while the indole is accumulated in the medium.

For development of these four tests, three test tubes were prepared for each agar medium. For the Kovac reagent, the positive control, *E. coli*, produced a bright red colored compound on the surface of the culture medium. However, *P. ourofinensis* did not show this coloring, which means that the tryptophan was not hydrolyzed and, therefore, the *P. ourofinensis* is classified as indole-negative. It was also verified that the *P. ourofinensis* isolate secretes substances able to digest the starch forming a halo when added to iodine. The test using media to demonstrate the fermentative catabolism (anaerobic) resulted in a yellow color to *E. coli* (positive control) and to the *P. ourofinensis* in glycerol, D-xylose, glucose, arabinose and no sugar, which means that there was fermentative degradation of the carbohydrates. Nitrate to nitrite reduction was noted in *E. coli* and in *P. ourofinensis* in view of the reaction in the presence of sulfanilic acid and N—N-dimethyl-1-naphthylamine producing red color, which indicates the presence of $NO_2$. In the casein test, *P. ourofinensis* was able to use the medium as nutrient, similar to *B. subtilis*. However, *E. coli* did not show this ability. In the test with KOH fast method (cell wall lyses), the *E. coli* strain showed formation of a viscous film (gram negative) due to the DNA release in saline solution. Whilst *P. ourofinensis* did not increase the viscosity, which means it is gram-positive.

It has been found that: (i) the new isolate is anaerobic optional; (ii) the colonies grown on LB medium agar are circular, irregular, shiny, convex and sticky; (iii) in agar agar Middlebrook, the colonies had circular to slightly irregular shape, slightly glossy, yellow light and sticky; (iv) the bacterial growth temperature is 28-37° C. and growth occurs at pH 7.0-8.0; (V) the isolate also grows in the presence of NaCl 2% and 5% after 24 hours in LB culture medium and approximately 48 h in TSA culture medium; (vi) when grown in both liquid culture medium (LB and TSA), the colonies formed whitish lumps; (vii) the isolate shows catalase-negative, oxidase-negative, and indole is not produced. Note that all other *Paenibacillus* genus species listed in Table 1 show positive catalase while the new isolate is negative in this test. Therefore, it can be concluded that the isolate inhibits the growth of *E. coli, Bacillus subtilis, Salmonella enteritidis* and produces an antimicrobial component.

The references cited in Table 1 are: (a) Kim et al., 204=Kim, Dal-Soo., Cheol-Yong Bae, Jae-Jin Jeon, Sam-Jae Chun, Hyun Woo Oh, Soon Gyu Hong, Keun-Sik Baek, Eun Young Moon & Kyung Sook Bae. 2004. *Paenibacillus elgii* sp. nov., with broad antimicrobial activity. *Int J Syst Evol Microbiol.* 54: 2031-2035; (b) Kuroshima et al., 1996=Kuroshima, K., Sakane, T., Takata, R. & Yokota, A. 1996. *Bacillus ehimensis* sp. nov. and *Bacillus chitinolyticus* sp. nov., new chitinolytic members of the genus *Bacillus*. Int J Syst Bacteriol. 46: 76-80; (c) Hendryckx et al., 1995=Heyndrickx M., Vandemeulebroecke K., Scheldeman P., Hoste B., Kersters K., De Vos P., Logan N. A., Aziz A. M., Ali N., Berkeley R. C. 1995. *Paenibacillus* (formerly *Bacillus*) *gordonae* (Pichinoty et al. 1986) Ash et al. 1994 is a later subjective synonym of *Paenibacillus* (formerly *Bacillus*) *validus* (Nakamura 1984) Ash et al. 1994: emended description of *P. validus. Int J Syst Bacteriol.* 45(4):661-669; (d) Chung et al., 2000=Chung, Y. R., Kim, C. H., Hwang, I. & Chun, J. 2000. *Paenibacillus koreensis* sp. nov., a new species that produces an iturin-like antifungal compound. *Int J Syst Evol Microbiol.* 50: 1495-1500; (e) Meehan et al., 2000=Meehan, C., Bijourson, A. J. & Mcmullan, G. 2001. *Paenibacillus azoreducens* sp. nov., a synthetic azo dye decolorizing bacterium from industrial wastewater. *Int J Syst Evol Microbiol.* 51: 1681-1685.

TABLE 1

Metabolic Properties of Paenibacillus

| Characteristc | P. ourofinensis | P. elgii | P. ehimensis | P. validus | P. koreensis | P. azoreducens |
|---|---|---|---|---|---|---|
| Catalase | − | + | + | + | + | + |
| Anaerobic Growth | + | + | − | − | + | + |
| Oxidase | − | − | + | − | + | − |
| Nitrate production | + | + | + | − | + | − |
| Indole production | − | + | NT | + | − | − |
| Casein hydrolysis | + | + | + | − | + | − |
| Growth in pH 5.6 | − | + | NT | + | + | |
| Growth at 50° C. | − | − | + | + | + | + |
| Growth in NaCl 5% | + | − | NT | NT | + | − |
| L-arabinose | − | + | − | + | − | |
| D-xylose | + | V | + | + | − | + |
| Glycerol | V | NT | NT | NT | + | |
| Growth in Lysozyme 0.001% | + | NT | NT | NT | + | NT |

(+) = positive;
(−) = negative;
(V) = variable;
(NT) = non-tested.
Species: *Paenibacillus elgii sp.* No. (Kim et al., 2004); *Paenibacillus ehimensis* IFO 15659$^T$ (Kuroshima et al., 1996); *Paenibacillus validus* (Heyndrickx et al., 1995); *Paenibacillus koreensis* KCTC 2393T (Chung et al., 2000); *Paenibacillus azoreducens* DSM 13822$^T$ (Meehan et al., 2001).

In addition, the characterization of *P. elgii ourofinensis* was achieved by means of molecular tools; among them are the Ribosomal Intergenic Space Analysis (RISA), the Identification of Random Amplified Polymorphic DNA (RAPD) and analysis of the gene rpoB sequence for studies of phylogenetic relationships. Further, the quantitative and qualitative differences in composition of fatty acids in cell walls was studied.

Analysis of Fatty Acids Methyl-Esters

To obtain the profile of *P. elgii ourofinensis*, the analysis of fatty acids methyl-esters (FAME) was performed from the bacterial cell (total fatty acids). The fatty acids were then analyzed by a microbial identification program (MIDI, Sherlock® Library TSBA 50 5.00) and the fatty acid profiles were compared to data from this library. MIDI analyzes more than 300 fatty acids and related compounds found in bacteria.

The profile of *P. ourofinensis* fatty acids is presented in Table 2.

TABLE 2

Profile of P. ourofinensis fatty acids

| RT | Response | Ar/Ht | RFact | ECL | Peak Name | % | Comment1 | Comment2 |
|---|---|---|---|---|---|---|---|---|
| 1.650 | 5.134E+8 | 0.035 | — | 6.957 | SOLVENT PEAK | — | <min RT | |
| 4.967 | 662 | 0.034 | 1.022 | 12.169 | 11:0 2OH | 0.49 | ECL deviates 0.009 | |
| 6.769 | 4115 | 0.038 | 0.996 | 13.618 | 14:0 ISO | 2.94 | ECL deviates −0.001 | Reference-0.002 |
| 7.291 | 1980 | 0.042 | 0.989 | 13.999 | 14:0 | 1.41 | ECL deviates −0.001 | Reference-0.003 |
| 8.254 | 8516 | 0.040 | 0.980 | 14.624 | 15:0 ISO | 5.99 | ECL deviates 0.001 | Reference-0.001 |
| 8.396 | 76805 | 0.041 | 0.978 | 14.715 | 15:0 ANTEISO | 53.95 | ECL deviates 0.002 | Reference 0.000 |
| 9.487 | 2881 | 0.043 | 0.969 | 15.389 | 16:1 w7c alcohol | 2.01 | ECL deviates 0.002 | |
| 9.652 | 680 | 0.045 | 0.968 | 15.488 | Sum In Feature 2 | 0.47 | ECL deviates 0.000 | 14:0 3OH/16:1 ISOI |
| 9.760 | 717 | 0.043 | 0.967 | 15.552 | 16:0 N alcohol | 0.50 | ECL deviates 0.002 | |
| 9.886 | 10645 | 0.043 | 0.967 | 15.628 | 16:0 ISO | 7.39 | ECL deviates 0.001 | Reference-0.002 |
| 10.107 | 6836 | 0.043 | 0.965 | 15.759 | 16:1 w11c | 4.74 | ECL deviates 0.002 | |
| 10.508 | 5890 | 0.043 | 0.963 | 15.999 | 16:0 | 4.07 | ECL deviates −0.001 | Reference-0.004 |
| 10.743 | 886 | 0.052 | 0.962 | 16.134 | 15:0 ISO 3OH | 0.61 | ECL deviates 0.000 | |
| 10.902 | 861 | 0.043 | 0.961 | 16.225 | 15:0 2OH | 0.59 | ECL deviates 0.006 | |

TABLE 2-continued

Profile of P. ourofinensis fatty acids

| RT | Response | Ar/Ht | RFact | ECL | Peak Name | % | Comment1 | Comment2 |
|---|---|---|---|---|---|---|---|---|
| 11.190 | 1008 | 0.040 | 0.960 | 16.390 | ISO 17:1 w10c | 0.70 | ECL deviates 0.002 | |
| 11.369 | 2261 | 0.070 | 0.960 | 16.493 | Sum In Feature 4 | 1.56 | ECL deviates 0.007 | 17:1 ANTEISO B/iI |
| 11.606 | 2229 | 0.048 | 0.959 | 16.629 | 17:0 ISO | 1.54 | ECL deviates −0.001 | Reference-0.003 |
| 11.768 | 7595 | 0.048 | 0.958 | 16.722 | 17:0 ANTEISO | 5.23 | ECL deviates −0.001 | Reference-0.003 |
| 12.517 | 2267 | 0.052 | 0.957 | 17.149 | 16:0 ISO 3OH | 1.56 | ECL deviates −0.001 | |
| 13.174 | 3332 | 0.048 | 0.958 | 17.519 | 16:0 3OH | 2.29 | ECL deviates 0.000 | |
| 14.313 | 1022 | 0.052 | 0.961 | 18.162 | 17:0 ISO 3OH | 0.71 | ECL deviates 0.001 | Reference 0.000 |
| 14.481 | 1828 | 0.051 | 0.962 | 18.257 | 17:0 2OH | 1.26 | ECL deviates 0.003 | |
| — | 680 | — | — | — | Summed Feature 2 | 0.47 | 12:0 ALDE ? | unknown 10.928 |
| — | 2261 | — | — | — | Summed Feature 4 | 1.56 | 17:1 ISO I/ANTEI B | 17:1 ANTEISO B/iI |

The comparison of results obtained with other species from the same genus is provided in Table 3.

TABLE 3

Total composition of P. ourofinensis fatty acids and comparison with strains from the same genus according to Kim et al., 2004.

| Fatty acids | P. ourofinensis | P. elgii SD17 | P. elgii SD18 | P. ehimensis | P. validus | P. koreensis | P. azoreducens |
|---|---|---|---|---|---|---|---|
| Saturated | | | | | | | |
| C14:0 | 1.4 | 1.9 | 1.0 | 1.0 | 2.1 (1.8-2.5) | 1.2 | 3.5 |
| C15:0 | 0.6 | 1.2 | 1.0 | 1.2 | 0.9 (0.8-1.1) | 0.8 | 0.1 |
| C16:0 | 4.1 | 9.7 | 6.2 | 7.1 | 5.6 (5.4-5.6) | 8.5 | 22.1 |
| Branched | | | | | | | |
| iso-C14:0 | 2.9 | 2.1 | 1.3 | 1.8 | 3.4 (3.1-3.9) | 1.6 | 0.8 |
| iso-C15:0 | 6.0 | 10.6 | 13.7 | 8.1 | 10.3 (9.7-11.3) | 6.0 | 5.9 |
| anteiso-C15:0 | 54.0 | 54.1 | 62.0 | 52.9 | 51.9 (50.6-52.7) | 43.4 | 33.9 |
| iso-C16:0 | 7.4 | 6.5 | 3.6 | 8.6 | 7.2 (6.9-7.5) | 12.2 | 8.6 |
| iso-C17:0 | 1.5 | 3.2 | 2.6 | 3.3 | 2.7 (2.2-3.5) | 5.5 | 5.6 |
| anteiso-C17:0 | 5.2 | 6.2 | 6.1 | 8.0 | 4.5 (3.9-5.0) | 11.9 | 19.8 |
| Unsaturated | | | | | | | |
| C16:1W7c alcohol | 2.0 | ND | ND | 1.2 | 2.6 (2.5-2.7) | 1.4 | ND |
| C16:1W11c | 4.7 | 4.5 | 2.5 | 5.2 | 7.0 (6.7-7.6) | 5.4 | ND |

The preliminary identification using the MIDI library shows that the new strain belongs to the *Paenibacillus* genus, but cannot be clearly identified as a known species due to the low relative similarity (0.663) (Table 4). Quantitative (iso-C15:0) and qualitative (C16:1W7c alcohol) differences were noted between *P. ourofinensis* and its nearly neighbor *P. elgii*. This fact suggests that this new strain may properly be characterized as a new species.

TABLE 4

Similarity index using MIDI.

| Similarity Index (SI) | Species |
|---|---|
| 0.633 | Paenibacillus-validus (Bacillus gordonae) |
| 0.396 | Paenibacillus-polymyxa (Bacillus) |

Determination of P. ourofinensis GC Content

Additionally, to further confirm the novelty of the new isolate, the same was grown in a Petri dish containing solid LB medium. The inhibition test with *Bacillus subtilis* and the Gram stain test were carried out to confirm that there was no contamination before sending the strain to the reference center for identification of the new bacterial isolates, located in Belgium. Confirming the absence of contamination, the strain was grown in 1.5 ml of LB soft agar in cryotubes and was sent to the said center to perform the following analyzes: DNA/DNA hybridization with other species of the *Paenibacillus* genus and percentage of GC content. In addition to the *P. ourofinensis* culture, other cultures of *Paenibacillus elgii* LMG 24465, *Paenibacillus ehimensis* LMG 18048 and *Paenibacillus validus* LMG 11161 were analyzed. After obtaining the DNA, the determination of *P. ourofinensis* GC content was determined using HPLC technique. The percentage obtained was 53.4% and this value was the average of three independent analyzes from the same DNA sample. DNA-DNA hybridizations were carried out at 44° C. and the homologies reported in the Table 5 are the average of at least two hybridizations. The mean standard deviation was 14 units, but deviations of 20-25 units were still accepted. The strain sent by us showed a homology superior to 70%, the limit accepted in general for delineation of species with *P. elgii* LMG 24465 type of strain. From this result, it could be concluded that the strain sent by us belongs to the species *Paenibacillus elgii*. However, While not wishing to be constrained by theory, we believe that *P. ourofinensis* may be a subspecies of *P. elgii* not identified previously.

TABLE 5

Result of DNA-DNA hybridization between strains in homology percentage.

| Strains | % DNA homology | | | |
|---|---|---|---|---|
| *P. ourofinensis* | 100 | 76 | 54 | 19 |
| *Paenibacillus elgii* | 111 | 100 | 55 | 11 |
| *Paenibacillus ehimensis* | 56 | 68 | 100 | 12 |
| *Paenibacillus validus* | 6 | 8 | 13 | 100 |

*P. elgii* and *P. ourofinensis* Comparison

Figure 12:
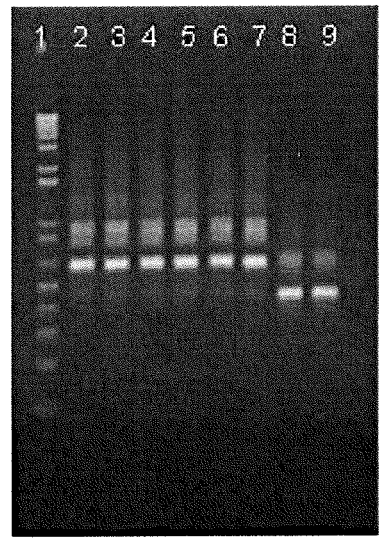
FIG. 12 is a photograph of UV florescence following electrophoresis of the DNA amplified by PCR with the primers 1406F/23SR in agarose gel. 1) Marker Ladder 1 kb plus; 2 and 3) *P. elgii;* 4 and 5) *P. ourofinensis;* 6 and 7) *Paenibacillus* sp.; 8 and 9) *Bacillus subtillis*.
Figure 13:
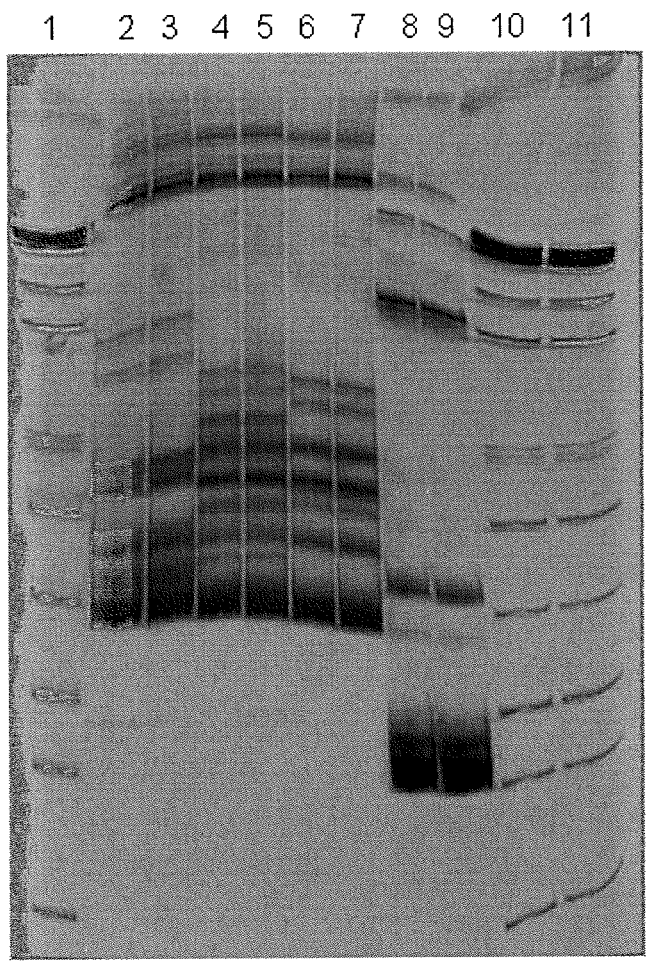
FIG. 13 is a photograph of a Ribosomal Intergenic Space Analysis in 6% polyacrylamide gel stained with silver nitrate. 1) Marker Ladder 1 kb plus; 2 and 3) *P. elgii;* 4 and 5) *P. ourofinensis;* 6 and 7) *Paenibacillus* sp.; 8 and 9) *Bacillus subtillis,* 10 and 11) Marker Ladder 1 kb plus

The *Paenibacillus elgii ourofinensis* strain was compared to the *Paenibacillus elgii* strain LGM 24465$^T$, KCTC10016BP, NBRC100335$^T$ obtained by the Bacteria Collection Laboratorium Voor Microbiologic in Belgium. DNA from *P. elgii*, *P. ourofinensis*, *Paenibacillus* sp. and *Bacillus subtillis* was extracted by the extraction kit MOBIO UltraClean™ Microbial DNA Isolation kit. A PCR was performed with 1406F/L1R (SEQ ID NOS: 7 and 9, respectively) oligonucleotides that amplify the ITS region (intergenic space region between the coded regions of ribosomal RNA's 16S and 23S). After verification of the PCR result, the product was submitted to electrophoresis in 6% polyacrylamide gel during 1 hour and 30 minutes under constant power of 45 W. Such analysis were performed repeatedly to confirm the veracity of the results. The result of the amplification of microorganisms DNA with the oligonucleotides 1406F/23SR (SEQ ID NOS: 7 and 8, respectively) is shown in FIG. 12. It could be noted in the duplicate testes, that the product fragments for *P. elgii*, *P. ourofinensis* and *Paenibacillus* sp. have the same size and that the *B. subtillis* amplified product has a different size. In the polyacrylamide gel (FIG. 13), the samples are also in duplicate to confirm the veracity of results, besides the fact that amplification and RISA had being carried out three times. As shown in FIG. 13, *P. elgii* sample presents a bands pattern very different from *P. ourofinensis*, although some equivalent bands. On the other hand, the *P. ourofinensis* and *Paenibacillus* sp. isolate show a very similar bands pattern, with few different bands. It could be noted that the bands pattern from the *Paenibacillus* genus is totally different from the *Bacillus* bands pattern. This result showed that *P. elgii* and *P. ourofinensis* show clear difference between them when analyzing their intergenic regions. Each strand showed in the gel may be representing a ribosomal operon that served as mold to amplify the intergenic region, and thus, these two strains have different operons, confirming that there are differences between *P. elgii* strains from the Bacteria Collection Laboratorium Voor Microbiologic and the *P. ourofinensis* isolated from Brazilian cerrado, which corresponds to the bacteria from which the extracts and the compounds of the invention are obtained.

Figure 14:
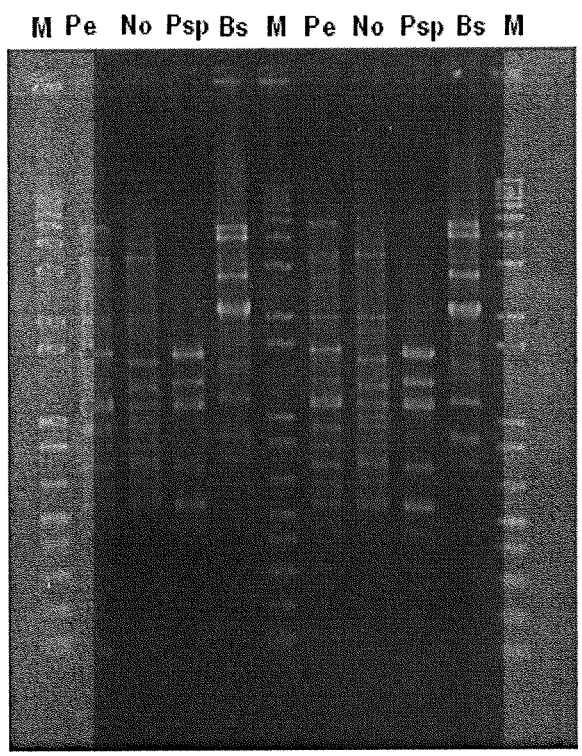
FIG. 14 is a photograph of UV florescence of the reaction product from RAPD amplification with the primer 208 following electrophoresis in 1% agarose gel in duplicate. (M=marker Ladder 1 kb plus; Pe=*P. elgii;* Po=*P. ourofinensis;* Psp=*Paenibacillus* sp. and Bs=*B. subtillis*).

Differences were also noted in RAPD analyses comparing *P. elgii*, *P. ourofinensis*, *Paenibacillus* sp. and *Bacillus subtillis* (FIG. 14). Again, it is noted that the band profile of *B. subtillis* DNA is totally different from the others. In the case of the *Paenibacillus* sp., the profile is different, however, some bands in common with the other *Paenibacillus* are noted, and there is a band in common for *P. elgii* and *Paenibacillus* sp. that is absent in the *P. ourofinensis* profile. When comparing the *P. elgii* and *P. ourofinensis* band profiles, it was noted the absence of strands in one sample and presence in the other as well as differences in intensity of some bands, however, the band profiles from these two strains are very similar between them, existing several bands in common.

RAPD

The RAPD technique allows the use of oligonucleotide primers with low stringency and few nucleotides, which arbitrarily select the sequences of specific sites from genomic DNA, where there is complete or semi-complete pairing from the amplified DNA, allowing distinction of samples from the same species by comparison of the genomic pattern obtained. This is one of the most simple methods, since the DNA mold is not required to be high molecular weight or highly purified, being necessary only some nanograms of the sample to perform the RAPD (Welsh & McClelland, 1990; Kersulyte et al., 1995). Then, the use of this technique to compare *P. elgii* and *P. ourofinensis* was important to show some differences between them, although they belong to the same species in view of the other analysis.

rpoB Gene Sequencing Analysis

To identify the *P. ourofinensis* isolate, a DNA extraction was carried out wherein the isolate was cultivated in conventional culture conditions, for example, LB medium, at 37° C. for 16 hours. The total DNA was extracted using a protocol based on cell lysis with solid carbon dioxide at 65° C. For the analysis of the 16S gene from the ribosomal DNA, an amplification reaction was carried out using the primers oligonucleotides 27F (SEQ. ID. NO: 1) and 1492R (SEQ ID. NO: 2). A PCR reaction was performed with the oligonucleotides 1698F (SEQ. ID. NO: 3) and 2041R (SEQ. ID. NO: 4), which are specific to the rpoB gene, highly conserved, which encode the RNA polymerase β subunit of bacteria. From the amplification products, both from rpoB gene and 16S gene, a ligation reaction to the vector pGEM-T Easy was made using the enzyme $T_4$ ligase (5 µl of buffer 10×, 3 µl of DNA; 1 µl of the vector pGEM-T Easy; 1 µl of $T_4$ Ligase). This reaction remained overnight in thermocycler at 16° C. and the enzyme was inactivated at 65° C. for 20 min. The linkage system was dialyzed for 30 min.

Transformations were carried out into *Escherichia coli* cells (DH5a). In this procedure, 10 µl of the linkage system and 50 µl of *E. coli* cells (DH5a) were submitted to electroporation, after that, 1 ml of SOC medium was added. After incubation for 1 h at 37° C., the cell suspension was plated in a petri plate with LB medium containing ampicillin (150 µg/ml), since the plasmid pGEM-T has genes resistant to this antibiotic. The suspension was incubated for 16 h in an incubator at 37° C. After the incubation, the plasmid DNA extraction was carried out in a Mini-prep with Qiagen kit. The plasmid DNA was digested with the restriction enzyme EcoRI and analyzed by electrophoresis in 1% agarose gel to verify the cloning. To analyze the 16S sequencing region, the plasmid DNA was submitted to sequencing reactions using the 27F oligonucleotide (SEQ ID. NO: 1). The partial sequence obtained from the 16S ribosomal RNA encoding gene of *P. ourofinensis* was filed in the GenBank database under the access number EU257517. For the rpoB gene, sequencing was carried out with two PCR reactions using the DNA plasmid, one with the oligonucleotides primers T7 (SEQ ID. NO: 5)/SP6 (SEQ ID. NO: 6), and the other, with the oligonucleotides set 1698F (SEQ ID. NO: 3)/2041R (SEQ ID. NO: 4). The partial sequence obtained from the rpoB gene of *P. ourofinensis* was also filed in the GenBank under the access number EU257518.

DNA from *P. elgii* was amplified by PCR using the primers 1698F (SEQ ID. NO: 3)/2041R (SEQ ID. NO: 4), which are specific to amplify the highly conserved rpoB gene, which encodes the subunit β from bacterial polymerase RNA. From the PCR product, a ligation reaction to a vector pGEM-T Easy by the enzyme $T_4$ ligase (5 n1 of buffer 10×, 3 μl of DNA; 1 μl of the vector pGEM-T Easy; 1 μl of $T_4$ Ligase) was performed. This reaction remained overnight in thermocycler at 16° C. ant the enzyme was inactivated at 65° C. for 20 min. The linkage system was dialyzed for 30 min. The transformation was carried out into *Escherichia coli* cells (Epi 300).

In this procedure, 10 μl of the linkage system and 50 μl of *E. coli* cells were submitted to electroporation, after that, 1 ml of SOC medium was added. After incubation for 1 h at 37° C., the cell suspension were plated in petri plate with LB medium containing ampicillin (150 μg/ml), since the plasmid pGEM-T has genes resistant to this antibiotic, and incubated for 16 h in an incubator at 37° C. Then, the plasmid DNA extraction was carried out in a Mini-prep with Qiagen kit. The plasmid DNA was digested with the restriction enzyme EcoRI and analyzed by electrophoresis in 1% agarose gel to verify the insert and the vector. Two PCR reactions were performed with the Miniprep product, one with the oligonucleotide primers T7 (SEQ ID. NO: 5)/SP6 (SEQ ID. NO: 6) and the other with the oligonucleotides set 1698F (SEQ ID. NO: 3)/2041R (SEQ ID. NO: 4). The product of these reactions were sequenced. Sequences of the rpoB gene from other species of *Paenibacillus* were obtained by the National Center for Biotechnology Information (NCBI) website for alignment through the program BioEdit, and phylogenetic tree construction, program MEGA4 using p-distance and neighbor joining with bootstrap 1000. *Bacillus subtillis* was used as external group.

When comparing the sequences obtained from the 16S rRNA region encoding gene and the rpoB gene sequences with the data of non-redundant sequences from the NCBI, the *P. ourofinensis* was identified as within the *Paenibacillus* genus. The *Paenibacillus* genus isolate is constituted of variable Gram-positive bacteria, facultative anaerobic or strictly anaerobic, with white, opaque round shaped colonies.

Figure 15:
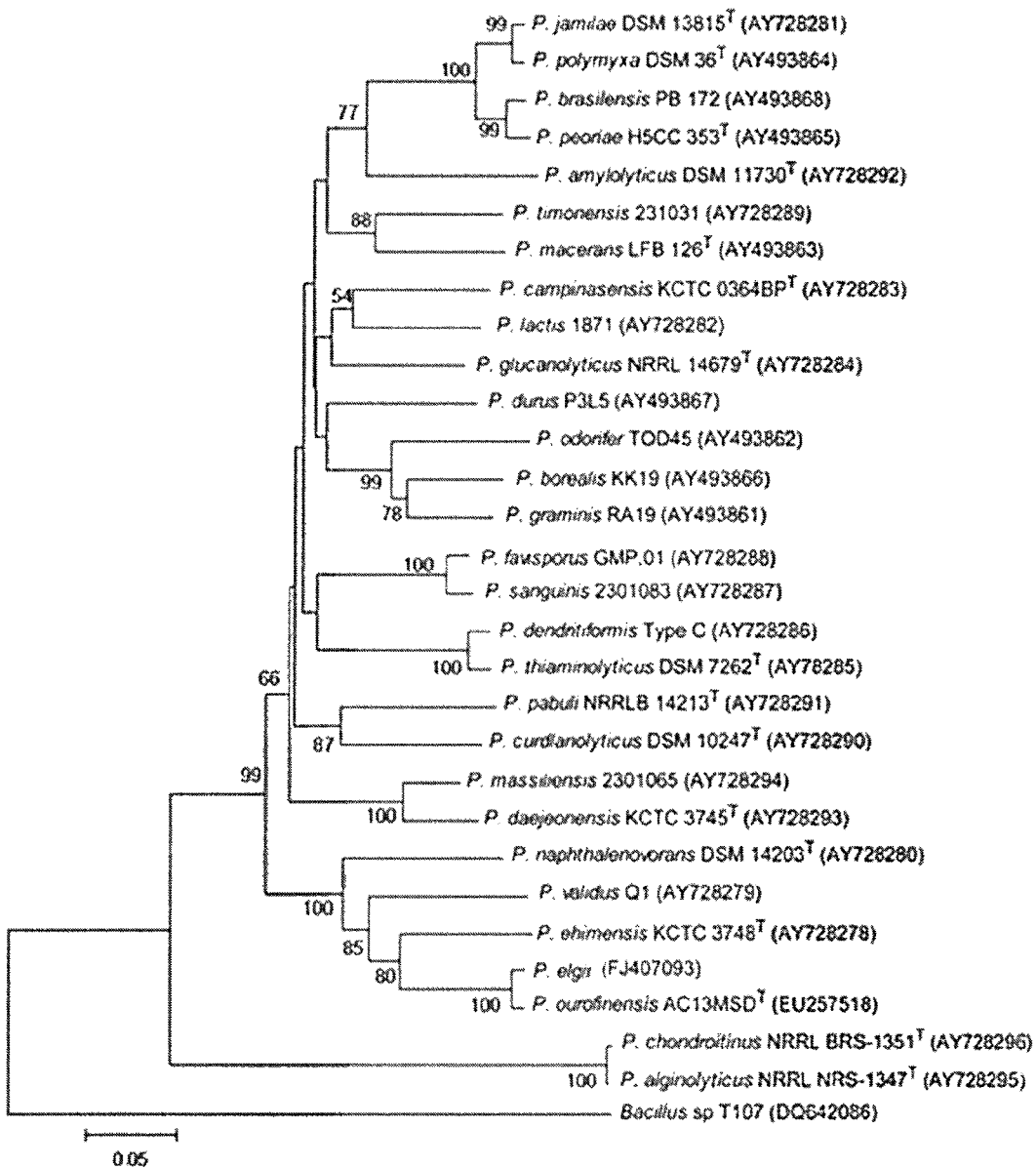
FIG. 15 is a cladogram of sequences of the rpoB gene obtained by the program MEGA 4 using Neighbor Joining-p-distance. Bootstrap=1000.

The result of the rpoB gene sequencing showed 98% identidy between *P. elgii* and *P. ourofinensis* sequences when analyzing the sequencing obtained from *P. elgii* by the program "nucleotide BLAST" (http://blast.ncbi.nlm.nih-.gov/Blast.cgi). Ther partial sequence of the rpoB gene was filed in the GenBank under the access number FJ407093. The phylogenetic tree shows extreme proximity between *P. elgii* and *P. ourofinensis* (FIG. 15). From the confirmation of this result, the isolate of the invention was called *Paenibacillus elgii ourofinensis*. Phylogenetic analyzes based on sequencing of rDNA 16S gene had great value to define the *Paenibacillus* genus (Ash et al., 1993). However, the limitations in phylogenetic analyzes based on rDNA 16S due to the presence of different copies of this gene restrict its use in *Paenibacillus* species (Berge et al., 2002). The rpoB gene has been used successfully to elaborate phylogenetic relationships in several groups of bacteria, and usually has a discriminatory power higher than the rDNA 16S sequences (Dahllof et al., 2000). The extreme similarity between the rpoB gene sequences from *P. elgii* and *P. ourofinensis* confirms the result of the DNA-DNA hybridization, which shows that the *P. ourofinensis* strain can be considered a subspecies, more specifically, a variation of the natural species *P. elgii*.

Example 3

*P. ourofinensis* Extract Activity

Lipopeptide resulting from n-butanol extraction of *Paenibacillus* fermentation broth, designated as LPPO below, may be used in the following formulations, for example for subsequent use as an additive for animal feed.

Compositions

TABLE 6

Spray dryer formulation

| Dry base composition | Preferred range % w/w | Acceptable range % w/w | Function |
|---|---|---|---|
| LPPO solid extract | 46.20* | 0.10-80.00 | Active ingredient |
| Xanthan gum | 0.00-0.50 | 0.00-2.00 | Stabilizer |
| HCl-Arginine | 0.00-0.50 | 0.00-1.00 | Stabilizer |
| Modified corn starch | 0.00-47.00 | 0.00-99.90 | Diluent |
| Silicon dioxide | 0.50 | 0.00-1.00 | Anti-wetting |
| Maltodextrin | to 100.00 | 0.00-99.90 | Diluent |
| Water** | 5.00-10.00 | 0.00-40.00 | Solvent |

*Considering that the extract has a LPPO content of 0.44% w/v wet base and a solid content of 4.62% w/w. The final LPPO content is 4.40% w/w.
**The amount of water is not considered in the formulation calculation due to its evaporation during the drying process.

Preparation:

Phase 1 a) In a proper container, add water and heat to 70° C., while stirring add: xantham gum, modified corn starch and maltodextrin and stir until moist.

b) Add arginine and homogenize.

Phase 2 a) Add the LPPO extract to a container.

b) Stir with a turrax at 13,000 rpm and add Phase 1.

c) Add silicon dioxide.

d) Stir for 5 minutes.

e) Keep stirring at approximately 90 rpm through the drying process.

Formulations Spray Dryer Drying Process Parameters:

a) Drying temperature: 130° C.

b) Atomizer diameter: 1 mm c) Input airflow: 60 $m^3$/h.

d) Feed flow: 5 g/min.

e) Atomizer pressure: 1 Kgf/$cm^2$.

Composition 2: Embedding to Rice Husk Fibers

| Dry base composition | Preferred range % w/w | Acceptable range % w/w | Function |
|---|---|---|---|
| LPPO solid extract | 5.59* | 0.10-100.00 | Active ingredient |
| Rice husk fiber 60/80 (350) | to 100.00 | 0.00-99.90 | Diluent |

*Considering that the extract has a LPPO content of 2.66% w/v wet base and solid content of 4.96% w/w. The final LPPO content will be 3.00% w/w.

Preparation:

1. In a mixer or a ribbon-type blender, add the rice husk fibers.

2. Stirring, add slowly the LPPO solution.
3. Start drying the mixture.
4. Collecting samples at specified periods until reaching the proper moisture and end the process.

A study was performed to evaluate the intestinal, hepatic and pancreatic morphometric parameters of chickens treated with PPO and probiotics as food additives against the antibiotics generally used. *P. elgii* was cultured in 2% Farmal medium, at pH 7.0, from 5 to 8 hours and then extracted by liquid-liquid extraction with n-butanol as described above.

1050 Ross chicks were fed until 42 days old with regular feed (T7) comprising corn, soybean bran, protein and energetic ingredients (ROSTAGNO et al. 2005) with or without additives. The chicks were separated in seven groups and each group was submitted to a different dietary regimen:

Control with no additive (T7);
Control with additive: T7+30 ppm of bacitracin zinc and 20 ppm of colistin;
Hydroenzime: T7+100 g of Hydroenzime (probiotic bacteria and enzymes);
Sympatic: T7+150 g of Sympatic (*Bacillus subtillis* QST-713 strain);
PPO 3 ppm: T7+3 ppm of *P. ourofinensis*;
PPO 6 ppm: T7+6 ppm of *P. ourofinensis*; and
PPO 9 ppm: T7+9 ppm of *P. ourofinensis*.

Small intestine, liver and pancreas samples were collected from 5 subjects of each group at age 21 and 42 days. The samples were properly treated and the following morphometric characteristics were evaluated. The villus height and length, crypt depth, number of villi, the ratio of villus high/crypt depth and goblet cells number of the small intestine; the area, perimeter, diameter and shape factor of the hepatocytes and the number of kupffer cells of the liver; and the area, diameter, perimeter and shape factor of the Langerhans cells and serous acinus of the pancreas. In addition, the small intestine of additional 21 subjects at 42 days old were collected and analyzed by Scanning electron microscope (Jeol JSM model).

It has been found that the intestinal parameters showed better results for the PPO 6 ppm regimen than the treatment with the Control with additive regimen, followed by the PPO 9 ppm and 3 ppm regimen; the hepatic parameters showed improved results over the Control with additive, Hydroenzime and sympatic regimens; and the pancreatic parameters showed improved results in the Hydroenzime, the Sympatic and the PPO 6 ppm regimens. Finally, in general, the PPO 6 ppm, Hydroenzime, Sympatic and the Control with additives regimens showed improved morphometric results. From the above stated it could be concluded that the *P. ourofinensis* extracts provides at least similar activity to the antibiotics and probiotic already know in the art, and therefore, may provide a viable alternative from those other regimens.

For the convenience of the reader, the sequences disclosed herein are summarized as follows:

| SEQ. ID. NO: | Oligonucleotide Designation | Sequence (5'-3') |
|---|---|---|
| 1 | 27F | AGAGTTTGATCMTGGCTCAG |
| 2 | 1492R | TACGGYTACCTTGTTACGACTT |
| 3 | 1698F | AACATCGGTTTGATCAAC |
| 4 | 2041R | GGTTGCATGTTGGTACCCAT |
| 5 | T7 | TAATACGACTCACTATAGGG |
| 6 | SP6 | ATTTAGGTGACACTATAG |
| 7 | 1406F | TGYACACACCGCCCGT |
| 8 | 23SR | GGGTTBCCCCATTCRG |
| 9 | L1R | CAAGGCATCCACCGT |
| 10 | 208 | ACGGCCGACC |

All publications and patent applications mentioned in the specification are indicative of the level of those skilled in the art to which the invention relates. All publications and patent applications are incorporated herein by way of reference to the same extent as if each individual publication or each patent application were specifically and individually indicated to be incorporated by way of reference.

Although the foregoing invention has been described in some detail by means of illustration and examples for purposes of clarity and understanding, it will be obvious that certain changes and modifications may be practiced within the scope of the claims accompanying this description.

The invention claimed is:

1. A method of preparing an extract containing lipopeptides, the method comprising fermenting a culture of *Paenibacillus elgii* and extracting at least one of the following lipopeptide compounds:

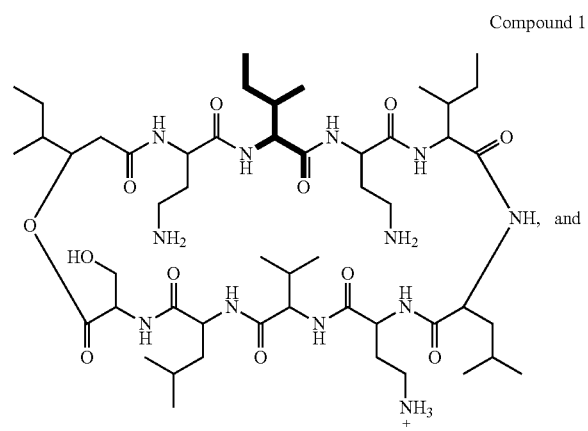

Compound 1

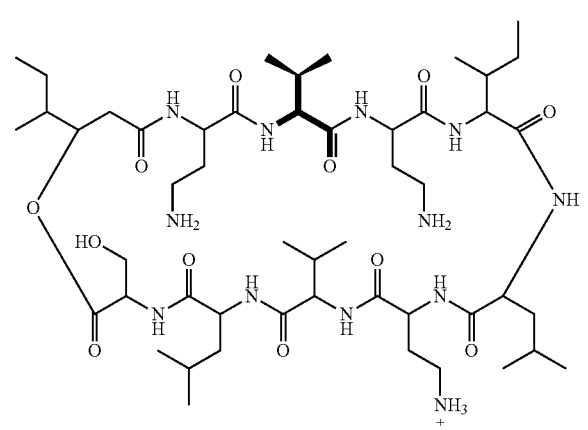

Compound 2 and wherein the extracting of at least one of Compounds 1 and 2 takes place by a butanol extraction, and additionally comprising drying the extract.

2. The method of claim 1, wherein the dried extract is combined with other nutritionally appropriate components to form an animal feed.

3. The method of claim 1, wherein the fermenting of *Paenibacillus* takes place in corn steep liquor medium.

4. The method of claim 3, wherein the corn steep liquor medium is 2% Famal medium at pH 7.0.

5. A method of isolating *Paenibacillus elgii ourofinensi*, the method comprising fermenting *Paenibacillus elgii* in a medium and isolating catalase negative bacteria.

6. The method of claim 5, wherein the medium is 2% corn steep liquor.

7. A method for the treatment of conditions caused by infections in animals or plants, the method comprising administering, to a plant or animal in need thereof, an effective amount of a lipopeptide selected from the group consisting of:

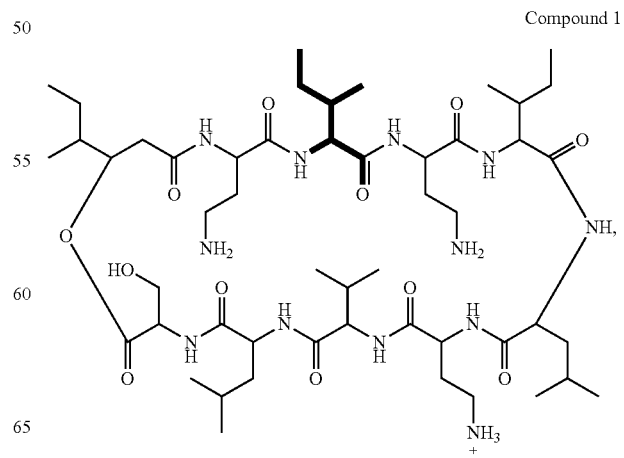

Compound 1

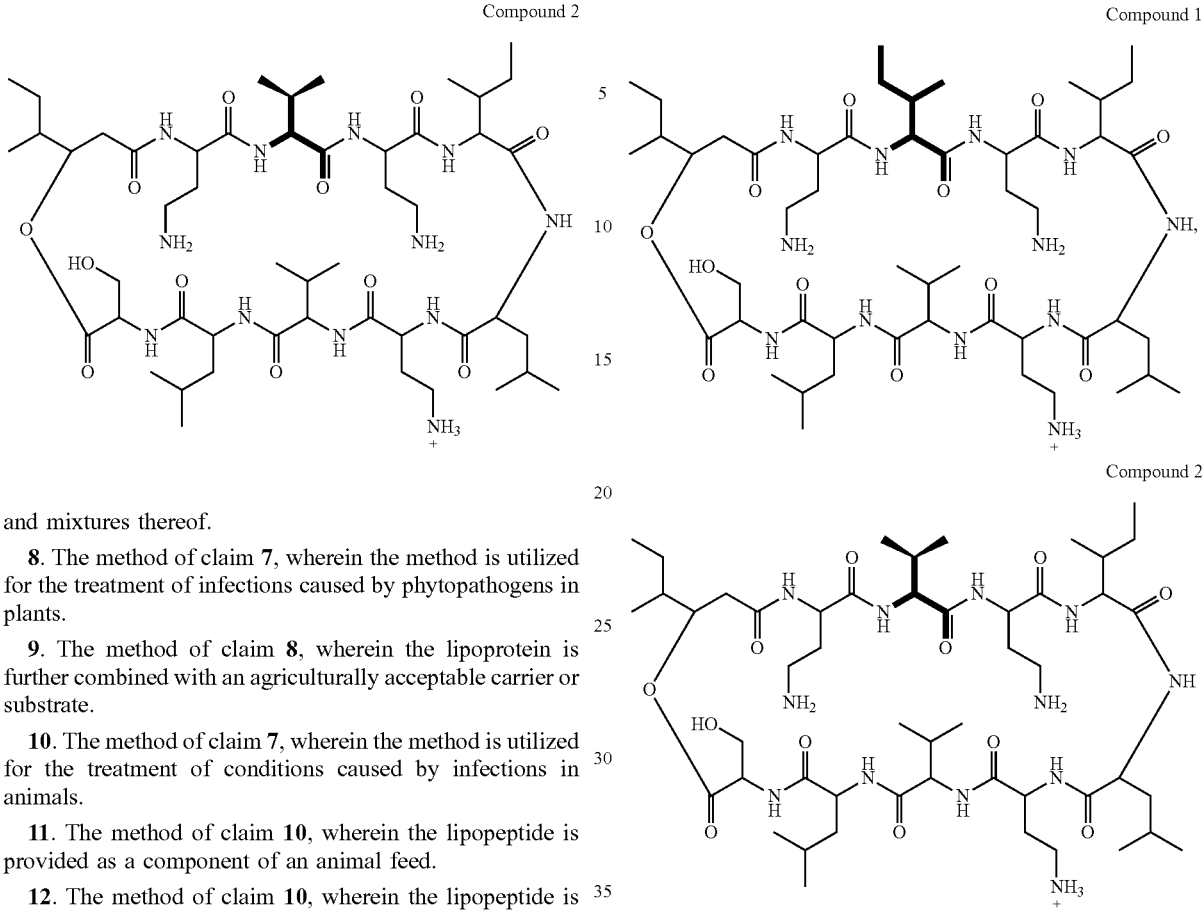

and mixtures thereof.

8. The method of claim 7, wherein the method is utilized for the treatment of infections caused by phytopathogens in plants.

9. The method of claim 8, wherein the lipoprotein is further combined with an agriculturally acceptable carrier or substrate.

10. The method of claim 7, wherein the method is utilized for the treatment of conditions caused by infections in animals.

11. The method of claim 10, wherein the lipopeptide is provided as a component of an animal feed.

12. The method of claim 10, wherein the lipopeptide is further combined with a therapeutic adjuvant.

13. The method of claim 12, wherein the lipopeptide is further combined with a pharmaceutically acceptable carrier or excipient.

14. The method of claim 10, wherein the lipopeptide is further combined with a pharmaceutically acceptable carrier or excipient.

15. The method of claim 1, wherein said culture of *Paenibacillus elgii* comprises *Paenibacillus elgii* ourofinensis.

16. A method for the prophylaxis of conditions caused by infections in animals or plants, the method comprising administering an effective amount of a lipopeptide selected from the group consisting of:

and mixtures thereof, to a plant or animal to receive prophylaxis.

17. The method of claim 16, wherein the method is utilized for the prophylaxis of infections caused by phytopathogens in plants.

18. The method of claim 16, wherein the method is utilized for the prophylaxis of conditions caused by infections in animals.

19. The method of claim 18, wherein the lipopeptide is provided as a component of an animal feed.

20. The method of claim 16, wherein the lipopeptide is further combined with a pharmaceutically acceptable carrier or excipient.

* * * * *

SEQUENCE LISTING

```
<160> NUMBER OF SEQ ID NOS: 10

<210> SEQ ID NO 1
<211> LENGTH: 20
<212> TYPE: DNA
<213> ORGANISM: Artificial Sequence
<220> FEATURE:
<223> OTHER INFORMATION: synthetic construct

<400> SEQUENCE: 1
agagtttgat cmtggctcag                                              20

<210> SEQ ID NO 2
<211> LENGTH: 22
<212> TYPE: DNA
<213> ORGANISM: Artificial Sequence
```

```
<220> FEATURE:
<223> OTHER INFORMATION: synthetic construct

<400> SEQUENCE: 2
tacggytacc ttgttacgac tt                                              22

<210> SEQ ID NO 3
<211> LENGTH: 18
<212> TYPE: DNA
<213> ORGANISM: Artificial Sequence
<220> FEATURE:
<223> OTHER INFORMATION: synthetic construct

<400> SEQUENCE: 3
aacatcggtt tgatcaac                                                   18

<210> SEQ ID NO 4
<211> LENGTH: 20
<212> TYPE: DNA
<213> ORGANISM: Artificial Sequence
<220> FEATURE:
<223> OTHER INFORMATION: synthetic construct

<400> SEQUENCE: 4
ggttgcatgt tggtacccat                                                 20

<210> SEQ ID NO 5
<211> LENGTH: 20
<212> TYPE: DNA
<213> ORGANISM: Artificial Sequence
<220> FEATURE:
<223> OTHER INFORMATION: synthetic construct

<400> SEQUENCE: 5
taatacgact cactataggg                                                 20

<210> SEQ ID NO 6
<211> LENGTH: 18
<212> TYPE: DNA
<213> ORGANISM: Artificial Sequence
<220> FEATURE:
<223> OTHER INFORMATION: synthetic construct

<400> SEQUENCE: 6
atttaggtga cactatag                                                   18

<210> SEQ ID NO 7
<211> LENGTH: 16
<212> TYPE: DNA
<213> ORGANISM: Artificial Sequence
<220> FEATURE:
<223> OTHER INFORMATION: synthetic construct

<400> SEQUENCE: 7
tgyacacacc gcccgt                                                     16

<210> SEQ ID NO 8
<211> LENGTH: 16
<212> TYPE: DNA
<213> ORGANISM: Artificial Sequence
<220> FEATURE:
<223> OTHER INFORMATION: synthetic construct

<400> SEQUENCE: 8
gggttbcccc attcrg                                                     16
```

```
<210> SEQ ID NO 9
<211> LENGTH: 15
<212> TYPE: DNA
<213> ORGANISM: Artificial Sequence
<220> FEATURE:
<223> OTHER INFORMATION: synthetic construct

<400> SEQUENCE: 9
caaggcatcc accgt                                                    15

<210> SEQ ID NO 10
<211> LENGTH: 10
<212> TYPE: DNA
<213> ORGANISM: Artificial Sequence
<220> FEATURE:
<223> OTHER INFORMATION: synthetic construct

<400> SEQUENCE: 10
acggccgacc                                                          10
```